(12) United States Patent
Cho et al.

(10) Patent No.: US 10,579,847 B2
(45) Date of Patent: Mar. 3, 2020

(54) ELECTRONIC DEVICE INCLUDING FINGERPRINT SENSOR AND OPERATING METHOD THEREOF

(71) Applicant: Samsung Electronics Co., Ltd., Gyeonggi-do (KR)

(72) Inventors: Gyu Sang Cho, Gyeonggi-do (KR); Hee Cheul Moon, Gyeonggi-do (KR); Hyung Dal Kim, Gyeonggi-do (KR); Kyung Hoon Song, Gyeonggi-do (KR); Kwang Sub Lee, Gyeonggi-do (KR); Se Young Jang, Gyeonggi-do (KR); Myung Su Kang, Seoul (KR); Heung Sik Shin, Jeollabuk-do (KR)

(73) Assignee: Samsung Electronics Co., Ltd (KR)

( * ) Notice: Subject to any disclaimer, the term of this patent is extended or adjusted under 35 U.S.C. 154(b) by 187 days.

(21) Appl. No.: 15/631,472

(22) Filed: Jun. 23, 2017

(65) Prior Publication Data

US 2017/0372114 A1 Dec. 28, 2017

(30) Foreign Application Priority Data

Jun. 24, 2016 (KR) .................... 10-2016-0079618

(51) Int. Cl.
*G06K 9/00* (2006.01)
*G01J 1/02* (2006.01)
(Continued)

(52) U.S. Cl.
CPC ........ *G06K 9/00006* (2013.01); *G01J 1/0219* (2013.01); *G01J 1/0233* (2013.01);
(Continued)

(58) Field of Classification Search
CPC .......... G06K 9/00006; G06K 9/00033; G06K 9/00114; G06K 9/00161; G01J 1/08;
(Continued)

(56) References Cited

U.S. PATENT DOCUMENTS 9,232,172 B2   1/2016  Perkins et al.
9,491,422 B2   11/2016 Perkins et al.
(Continued)

FOREIGN PATENT DOCUMENTS

EP    0045916        2/1982
WO    WO 2014/018121  1/2014
WO    WO 2015/192630  12/2015

OTHER PUBLICATIONS

European Search Report dated Apr. 11, 2018 issued in counterpart application No. 17177482.1-1231, 8 pages.
(Continued)

*Primary Examiner* — John B Strege
(74) *Attorney, Agent, or Firm* — The Farrell Law Firm, P.C.

(57) ABSTRACT

An electronic device is provided which includes a light emitting module that radiates infrared light, a window disposed on the light emitting module and having a specific refractive index with respect to the infrared light, wherein the window includes a refraction part that totally reflects the infrared light inside the window in correspondence with the specific refractive index, and a fingerprint sensor disposed under the window and obtaining a fingerprint of a user based on a user input on the window by using scattered light of the infrared light.

18 Claims, 31 Drawing Sheets

(51) Int. Cl.
- *G01J 1/08* (2006.01)
- *G01J 1/58* (2006.01)
- *G01J 5/10* (2006.01)
- *G06T 11/00* (2006.01)

(52) U.S. Cl.
CPC ............... *G01J 1/0266* (2013.01); *G01J 1/08* (2013.01); *G01J 1/58* (2013.01); *G01J 5/10* (2013.01); *G06K 9/00033* (2013.01); *G06K 9/00114* (2013.01); *G06K 9/00161* (2013.01); *G06T 11/003* (2013.01); *G01J 2001/0257* (2013.01); *G01N 2201/061* (2013.01); *G01N 2201/0638* (2013.01); *G06T 2207/10* (2013.01); *G06T 2207/10008* (2013.01); *G06T 2207/10048* (2013.01)

(58) Field of Classification Search
CPC .......... G01J 1/0233; G01J 1/58; G01J 1/0219; G01J 1/0266; G01J 5/10; G01J 2001/0257; G06F 3/0412; G06F 3/0421; G06F 2203/04109; G06T 11/003; G06T 2207/10008; G06T 2207/10; G06T 2207/10048; G01N 2201/061; G01N 2201/0638
See application file for complete search history.

(56) References Cited

U.S. PATENT DOCUMENTS

| | | | |
|---|---|---|---|
| 2007/0298332 A1* | 12/2007 | Han | G03F 1/36 430/5 |
| 2015/0104083 A1* | 4/2015 | Gu | G06K 9/0004 382/124 |
| 2015/0124175 A1 | 5/2015 | Perkins et al. | |
| 2015/0253931 A1* | 9/2015 | Wyrwas | G06F 3/0425 345/175 |
| 2016/0070404 A1 | 3/2016 | Kerr et al. | |
| 2016/0142686 A1 | 5/2016 | Perkins et al. | |
| 2016/0147128 A1 | 5/2016 | Loxley et al. | |
| 2016/0232397 A1* | 8/2016 | Yu | G06K 9/00053 |
| 2017/0193270 A1* | 7/2017 | Zhang | G02B 6/005 |

OTHER PUBLICATIONS

European Search Report dated Nov. 17, 2017 issued in counterpart application No. 17177482.1-1507, 10 pages.

\* cited by examiner

ELECTRONIC DEVICE INCLUDING FINGERPRINT SENSOR AND OPERATING METHOD THEREOF

PRIORITY

This application claims priority under 35 U.S.C. § 119(a) to Korean Patent Application Serial No. 10-2016-0079618, which was filed on Jun. 24, 2016 in the Korean Intellectual Property Office, the entire content of which is incorporated herein by reference.

BACKGROUND

1. Field of the Disclosure

The present disclosure generally relates to an electronic device, and more particularly, an electronic device including a fingerprint sensor.

2. Description of the Related Art

A conventional portable electronic device may include a fingerprint sensor. In the conventional electronic device which includes a fingerprint sensor, the fingerprint sensor is disposed in a periphery of a lower portion of a display area of the electronic device, in a housing of the electronic device, on a rear surface of a case, and the like, and supports a fingerprint authentication function by using the fingerprint sensor.

The above-described conventional fingerprint sensor may perform fingerprint recognition by emitting light from an area under the surface of the finger to the surface of the finger and collecting light reflected from the surface of the finger. As such, in the case where a foreign object is located in an area in which a fingerprint is sensed, an error in the fingerprint recognition may occur because the foreign object is recognized as a portion of one of the valleys or the ridges of the fingerprint. In addition, since the conventional fingerprint sensor includes a light emitting unit for sensing a fingerprint, the conventional fingerprint sensor is typically thick. Accordingly, it is difficult to make the electronic device slim.

SUMMARY

Aspects of the present disclosure are to address at least the above-mentioned problems and/or disadvantages and to provide at least the advantages described below. According to an aspect of the present disclosure, an electronic device is provided which includes a fingerprint sensor that disposes a light emitting module for fingerprint sensing at a location different from the location of a light receiving unit for the fingerprint sensing, and a method of operating the electronic device.

In accordance with an aspect of the present disclosure, an electronic device is provided which includes a light emitting module configured to radiate infrared light, a window disposed on the light emitting module and having a specific refractive index with respect to the infrared light, wherein the window includes a refraction part configured to totally reflect the infrared light inside the window in correspondence with the specific refractive index and a fingerprint sensor disposed under the window and configured to obtain a fingerprint of a user based on a user input on the window using scattered light of the infrared light.

In accordance with another aspect of the present disclosure, an electronic device is provided which includes a window having a first specific refractive index with respect to light, a light emitting module disposed on one surface of the window and configured to radiate infrared light such that the infrared light is totally reflected inside the window in correspondence with the first specified refractive index, a connection member having a second specified refractive index with respect to the light and is interposed between the window and the light emitting module and a fingerprint sensor disposed under the window and configured to obtain a fingerprint of a user based on a user input on the window using scattered light of the infrared light.

In accordance with another aspect of the present disclosure, a method of operating an electronic device is provided which includes receiving a user input, activating a light emitting module disposed in an area under a periphery of a window such that infrared light is emitted while being totally reflected toward an inside of the window, generating a fingerprint image by collecting the infrared light reflected on a surface of a finger disposed on the window while the infrared light is totally reflected inside the window and performing fingerprint authentication associated with the fingerprint image.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
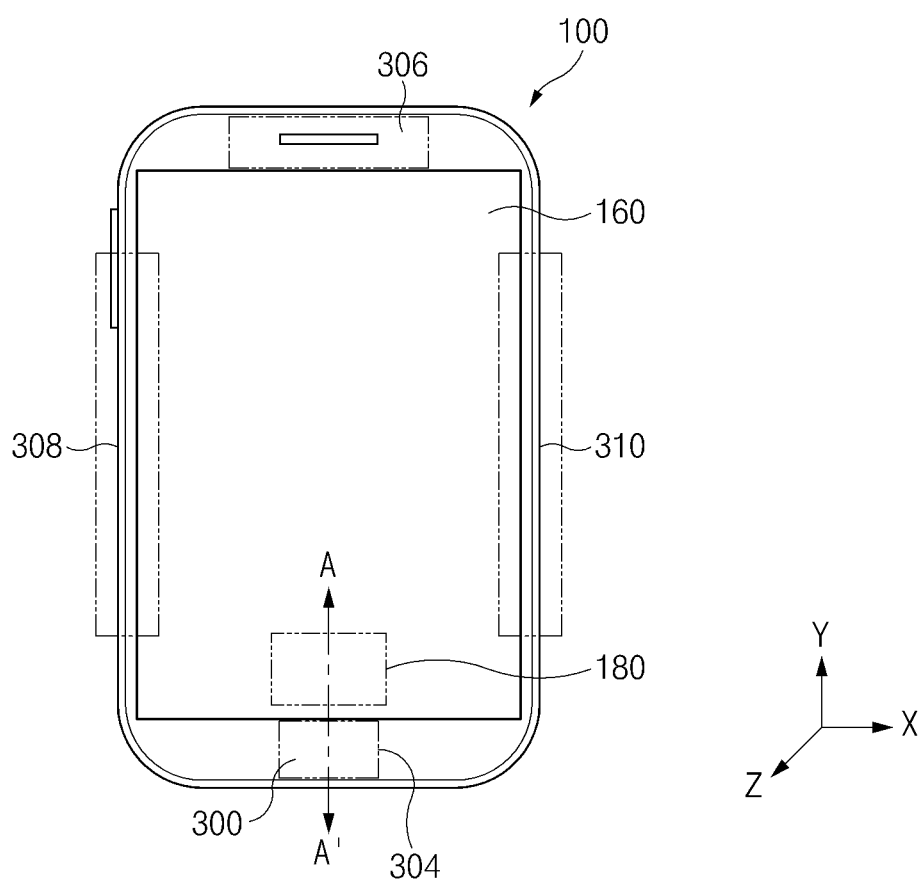
FIG. 1 illustrates an external appearance of an electronic device including a fingerprint sensor, according to an embodiment of the present disclosure.

Various embodiments of the present disclosure may be described with reference to the accompanying drawings. Accordingly, those of ordinary skill in the art will recognize that modifications, equivalents, and/or alternatives on the embodiments described herein can be made without departing from the scope and spirit of the present disclosure. With regard to the description of the drawings, similar elements may be marked by similar reference numerals.

In the present disclosure, the expressions "have", "may have", "include" and "comprise", or "may include" and "may comprise" as used herein indicate the existence of corresponding features (e.g., elements such as numeric values, functions, operations, or components) but do not exclude the presence of additional features.

In the present disclosure, the expressions "A or B", "at least one of A or/and B", or "one or more of A or/and B", and the like as used herein may include any and all combinations of one or more of the associated listed items. The terms "A or B", "at least one of A and B", or "at least one of A or B" may refer to all of the case (1) where at least one A is included, the case (2) where at least one B is included, or the case (3) where both of at least one A and at least one B are included.

The terms "first", "second", and the like as used herein may refer to various elements of an embodiment of the present disclosure, but do not limit the elements. Furthermore, such terms may be used to distinguish one element from another element. For example, "a first user device" and "a second user device" may indicate different user devices regardless of the order or priority thereof.

It will be understood that when an element (e.g., a first element) is referred to as being "(operatively or communicatively) coupled with/to" or "connected to" another element (e.g., a second element), it may be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening elements (e.g., a third element).

According to the situation, the expression "configured to" as used herein may be used interchangeably with the expressions "suitable for", "having the capacity to", "designed to", "adapted to", "made to", or "capable of". The term "configured to" does not mean only "specifically designed to" in hardware. Instead, the expression "a device configured to" may mean that the device is "capable of" operating together with another device or other components. A "processor configured to perform A, B, and C" may mean a dedicated processor (e.g., an embedded processor) for performing a corresponding operation or a general-purpose processor (e.g., a central processing unit (CPU) or an application processor) which may perform corresponding operations by executing one or more software programs which are stored in a memory device.

Terms used in the present disclosure are used to describe specific embodiments and do not limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal manner unless expressly so defined herein. In some cases, even if terms defined in the specification, they are not to be interpreted to exclude embodiments of the present disclosure.

An electronic device according to an embodiment of the present disclosure may include at least one of smartphones, tablet personal computers (PCs), mobile phones, video telephones, e-book readers, desktop PCs, laptop PCs, netbook computers, workstations, servers, personal digital assistants (PDAs), portable multimedia players (PMPs), motion picture experts group (MPEG-1 or MPEG-2) audio layer 3 (MP3) players, mobile medical devices, cameras, wearable devices (e.g., head-mounted-devices (HMDs), such as electronic glasses), an electronic apparel, electronic bracelets, electronic necklaces, electronic appcessories, electronic tattoos, smart watches, and the like.

According to an embodiment of the present disclosure, the electronic devices may be home appliances. The home appliances may include at least one of, for example, televisions (TVs), digital versatile disc (DVD) players, audio players, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to an embodiment of the present disclosure, the electronic device may include at least one of medical devices (e.g., various portable medical measurement devices (e.g., a blood glucose monitoring device, a heartbeat measuring device, a blood pressure measuring device, a body temperature measuring device, and the like)), a magnetic resonance angiography (MRA), a magnetic resonance imaging (MRI), a computed tomography (CT) machine, scanners, and ultrasonic devices), navigation devices, global positioning system (GPS) receivers, event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller machines (ATMs), point of sales (POS) terminals, or Internet of things (IoT) devices (e.g., light bulbs, various sensors, electric or gas meters, sprinkler devices, fire alarms, thermostats, street lamps, toasters, exercise equipment, hot water tanks, heaters, boilers, and the like).

According to an embodiment of the present disclosure, the electronic devices may include at least one of parts of furniture or buildings/structures, electronic boards, electronic signature receiving devices, projectors, or various measuring instruments (e.g., water meters, electricity meters, gas meters, or wave meters, and the like). The electronic device may be one of the above-described various devices or a combination thereof. An electronic device may be a flexible device. Furthermore, an electronic device may not be limited to the above-described electronic devices and may include other electronic devices and new electronic devices according to the development of new technologies.

Hereinafter, an electronic device according to an embodiment of the present disclosure, may be described with reference to the accompanying drawings. The term "user" as used herein may refer to a person who uses an electronic device or may refer to a device (e.g., an artificial intelligence electronic device) that uses an electronic device.

FIG. 1 illustrates an external appearance of an electronic device including a fingerprint sensor, according to an embodiment of the present disclosure.

Referring to FIG. 1, an electronic device 100 may have a tetragonal shape, and at least part of the corners of the electronic device 100 may be rounded. The electronic device 100 may have edges in which at least one of the sides of the electronic device 100 (e.g., a left side or a right side of the electronic device 100 with respect to a longitudinal arrangement state of a display 160) is gradually curved as it goes towards a periphery of the electronic device 100.

According to an embodiment of the present disclosure, a fingerprint sensor 180 that senses a fingerprint of a user contacting at least a partial area of the display 160 may be disposed in a space (e.g., a display pixel layer or thereunder) that is substantially vertical in a thickness direction (a z-axis direction) with respect to at least a partial area of an active area (or a display area) in which a screen of the display 160 is displayed. The fingerprint sensor 180 may have a specified size (e.g., a size corresponding to a technical and statistical size, by which the fingerprint of the user is capable of being recognized), and may be disposed on one side of a rear surface of the display 160. The fingerprint sensor 180 may include a light receiving unit.

Light for sensing the fingerprint of the fingerprint sensor 180 may be emitted from a light emitting module 300 (or a light emitter). The light emitting module 300 may be spaced apart from the fingerprint sensor 180 by a specified distance and may be disposed in at least one peripheral area of the electronic device 100. The light emitting module 300 may be disposed in at least one area of a lower portion area 304 (e.g., under a peripheral area with respect to a location at which the fingerprint sensor 180 is disposed), an upper portion area 306, a left side area 308, and a right side area 310 of the electronic device 100. The light emitted from the light emitting module 300 may be totally reflected through the inside of a window which is placed on the display 160 of the electronic device 100. As such, for example, if the light emitting module 300 is disposed in the lower portion area 304, the light emitted from the light emitting module 300 of the lower portion area 304 may be propagated while being totally reflected toward the window. If the light emitting module 300 is disposed in the left side area 308 (or the right side area 310 or the upper portion area 306) and the light is emitted from the light emitting module 300, the light may be propagated toward the window while being totally reflected toward the inside of the window.

According to an embodiment of the present disclosure, the fingerprint sensor 180 may be placed on a rear surface of the display and may obtain an image corresponding to the finger of the user through an opening (e.g., a hole area between a display cell and a pattern) included in the display (e.g., Y-OCTA: a display incorporated with touchscreen and display panel). The fingerprint sensor 180 may include an optical fingerprint sensor, and the optical fingerprint sensor may include various image signal processor (ISP) sensors such as a charge-coupled device (CCD) image sensor, a complementary metal-oxide-semiconductor (CMOS) image sensor, and the like. A method and a structure resolving an issue due to a foreign object on the sensor by using total internal reflection of the light emitted from the infra-red (IR) sensor-type light emitting module 300 may be included in the fingerprint sensor 180. The total internal reflection may include light having an incident angle greater than or equal to a critical angle reflected on a boundary surface between different media. The display 160 including the window may be provided such that at least a portion of the light emitted from the light emitting module 300 reaches a specified area of the window, while being totally reflected inside the window (or glass or an outer cover).

At least part of the display 160 may be formed to be transparent. The display 160 may have specific transparency (e.g., a ratio of the amount of light passing through the display to the amount of light emitted from a light source is in the range of 5 to 10%). Alternatively, the display 160 may be formed such that an area including at least part of an area in which the fingerprint sensor 180 is disposed is transparent. In this regard, the fingerprint sensor 180 may be placed under pixels of the display 160, and may collect and process light passing through transparent substrates in which pixels are disposed.

As described above, according to an embodiment of the present disclosure, in the electronic device 100, the fingerprint sensor 180 including a light receiving unit may be disposed under an active area (e.g., a specific area between a display area of the display 160 and the housing in which the display 160 is seated) of the display 160, and the light emitting module 300 may be disposed in a peripheral area of the electronic device 100. Accordingly, an increase in the thickness of the electronic device 100 may be minimized and a function associated with fingerprint sensing may be provided regardless of whether a foreign object is present on the sensor or the user's fingertip.

Figure 2A:
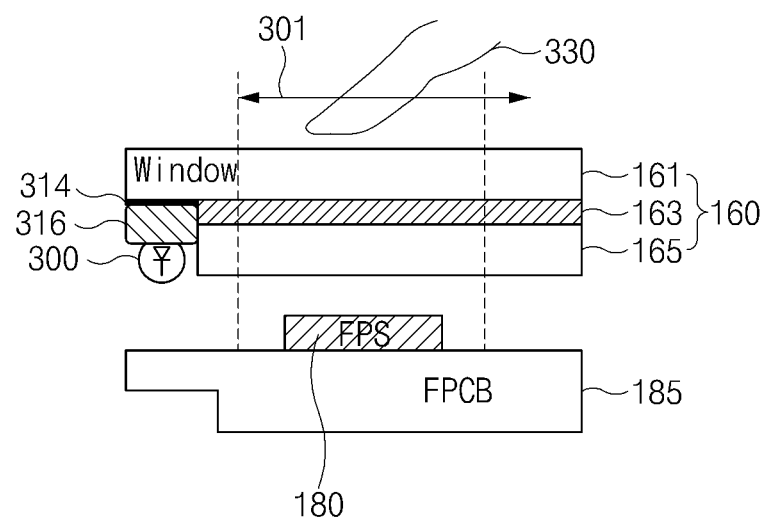
FIG. 2A illustrates a cross section of a part of an electronic device, according to an embodiment of the present disclosure.

FIG. 2A illustrates a cross section of a part of an electronic device, according to an embodiment of the present disclosure.

Referring to FIG. 2A, the electronic device 100 includes the display 160, the fingerprint sensor 180, a substrate 185, and the light emitting module 300. Additionally, the electronic device 100 may further include a case (or a housing) surrounding a side surface of the display 160.

The display 160 includes a window 161, a bonding layer 163, and a display panel 165. Alternatively, the display 160 may further include a printed layer. The printed layer may be disposed in a peripheral area of the display 160 and may be disposed on a layer the same as or similar to the bonding layer 163.

The window 161 may be disposed with specific thickness and width. The window 161 may be formed of transparent glass, transparent plastic, and the like. The window 161 may have a surface larger than the display panel 165. The bonding layer 163 may be at least partly disposed under the window 161 (e.g., a first area corresponding to a display area of a display panel). The light emitting module 300 may be disposed under one side (e.g., a second area corresponding to a non-display area, an area in which the printed layer is disposed, or an area in which the black matrix is disposed) of the window 161.

The bonding layer 163 (e.g., optical clear adhesive (OCA)) may bond the window 161 and the display panel 165. At least part of the bonding layer 163 may have a specific refractive index. The refractive index of the bonding layer 163 may be smaller than that of the window 161. As such, at least a portion of the light propagated through the window 161 may be totally reflected from a boundary surface between the window 161 and the bonding layer 163. The light which has a specific first angle and which is incident on the boundary surface between the window 161 and the bonding layer 163 may be totally reflected from the boundary surface. Alternatively, the light which has a specific second angle and which is incident on the boundary surface between the window 161 and the bonding layer 163 may be incident in a direction of the display panel 165 after passing through the bonding layer 163.

The display panel 165 may include a plurality of pixels disposed in a matrix form, wiring lines disposed to supply the electric power to the pixels, a substrate on which the pixels, wiring lines, and a display driver IC (DDI) are placed, and the like. At least a partial area of the display panel 165 may be formed to be transparent (or to have a specific transparency). The display panel 165 may have a specific transparency (e.g., 5 to 10%) such that light passes through gaps between wiring lines of the display panel 165. The display panel 165 may occupy at least part of a front surface of the electronic device 100. At least a portion of light passing through the bonding layer 163 may reach the fingerprint sensor 180 after passing through the display panel 165.

The fingerprint sensor 180 may be disposed in a specific area under the display 160. Based on the above-described structure, the fingerprint sensor 180 may sense a fingerprint of a finger touching a specific area of the display 160. According to an embodiment of the present disclosure, for example, the fingerprint sensor 180 may receive the light that is emitted from the light emitting module 300 and is reflected by an object placed in a fingerprint authentication area. The fingerprint authentication area may include an area of the display 160 in which the fingerprint sensor 180 is disposed. Alternatively, a minimum size area of the fingerprint authentication area may be set to an area of the display 160 facing the fingerprint sensor 180, and the fingerprint authentication area may include an area (an area set to be larger than an area corresponding to the size of the fingerprint sensor 180) of a specific size, which is touched by a finger of the user with respect to the area facing the fingerprint sensor 180.

If the light is collected by the fingerprint sensor 180, the fingerprint sensor 180 may generate image information corresponding to the collected light and may store the generated image information such that a processor (or an IC) disposed on the substrate 185 may use the generated image information. According to an embodiment of the present disclosure, the fingerprint sensor 180 may transmit an event (e.g., information indicating whether the image information is obtained) associated with obtaining the image information to a DDI. In this regard, the electronic device 100 may further include a signal line for transmitting the event between the fingerprint sensor 180 and the DDI. Alternatively, the fingerprint sensor 180 may transmit the collected image information to a processor through the main printed circuit board electrically connected with the substrate 185.

The fingerprint sensor 180 may be seated in the substrate 185. The substrate 185 may include at least one of a signal line or a power line that is associated with driving the fingerprint sensor 180. At least part of the substrate 185 may include a flexible substrate. A processor associated with the driving of the fingerprint sensor 180 may be mounted on the substrate 185. Alternatively, the substrate 185 may be electrically connected with the main printed circuit board on which the processor associated with the driving of the fingerprint sensor 180 is disposed. The substrate 185 may include the processor (or the IC) associated with the driving of the fingerprint sensor 180 and at least one signal line connecting the processor with the light emitting module 300. Alternatively, the substrate 185 may include at least one signal line electrically connecting the light emitting module 300 with the main printed circuit board.

The light emitting module 300 may be disposed under one side of the window 161. According to an embodiment of the present disclosure, the light emitting module 300 may be disposed on a layer the same as or similar to the display panel 165. The light emitting module 300 may emit light by using electric power supplied through the substrate 185 and may emit the light generated to the window 161. An adhesive member 314 may be interposed between the light emitting module 300 and the window 161. The adhesive member 314 may fix the light emitting module 300 and the window 161 and may have specific transparency such that the light emitted from the light emitting module 300 is incident on the window 161. A light guide member 316 (or a coupler, or a connection member) may be interposed between the light emitting module 300 and the adhesive member 314. The light guide member 316 may serve as a light path to allow the light emitted from the light emitting module 300 to be incident in a direction of the window 161. The light guide member 316 may have the specific transparency for light transmission. The light guide member 316 may be integrated with or may be bonded to the light emitting module 300. The light guide member 316 may be bonded to the window 161 based on the adhesive member 314.

As described above, in the electronic device 100, according to an embodiment of the present disclosure, while the incident light is totally reflected from a boundary surface between the window 161 and the bonding layer 163 or a boundary surface between the window 161 and an air layer on the window 161, after the light emitted from the light emitting module 300 is incident on the window 161, the light may be propagated to at least a partial area of the window 161.

Figure 2B:
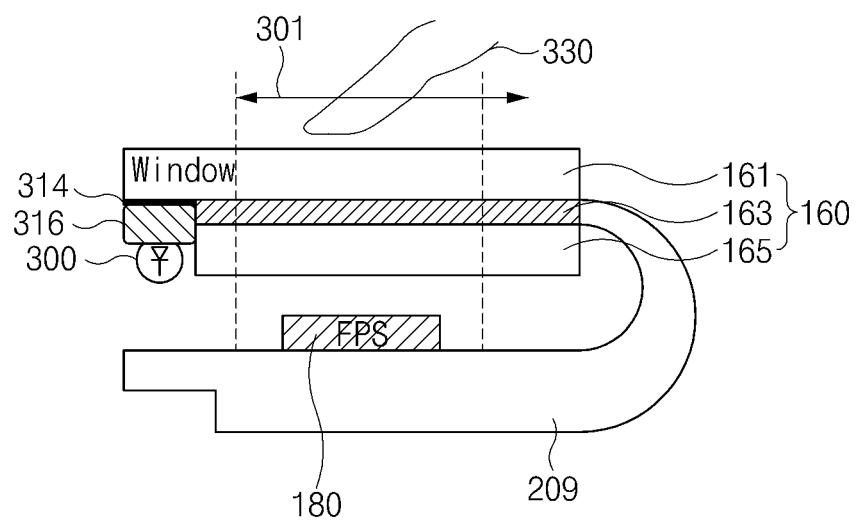
FIG. 2B illustrates a cross section of a part of an electronic device, according to another embodiment of the present disclosure.

FIG. 2B illustrates a part of a cross section of an electronic device, according to an embodiment of the present disclosure.

Referring to FIG. 2B, the electronic device 100 includes the display 160, the fingerprint sensor 180, a display substrate 209, and the light emitting module 300. Additionally, the electronic device 100 may further include a case (or a housing) surrounding a side surface of the display 160. The above-mentioned components may include the display substrate 209 (e.g., a flexible printed circuit board (FPCB)) connected to the display panel 165, and the fingerprint sensor 180 may be disposed on the display substrate 209. An IC associated with the driving of the fingerprint sensor 180 may be mounted on the display substrate 209.

Figure 3A:
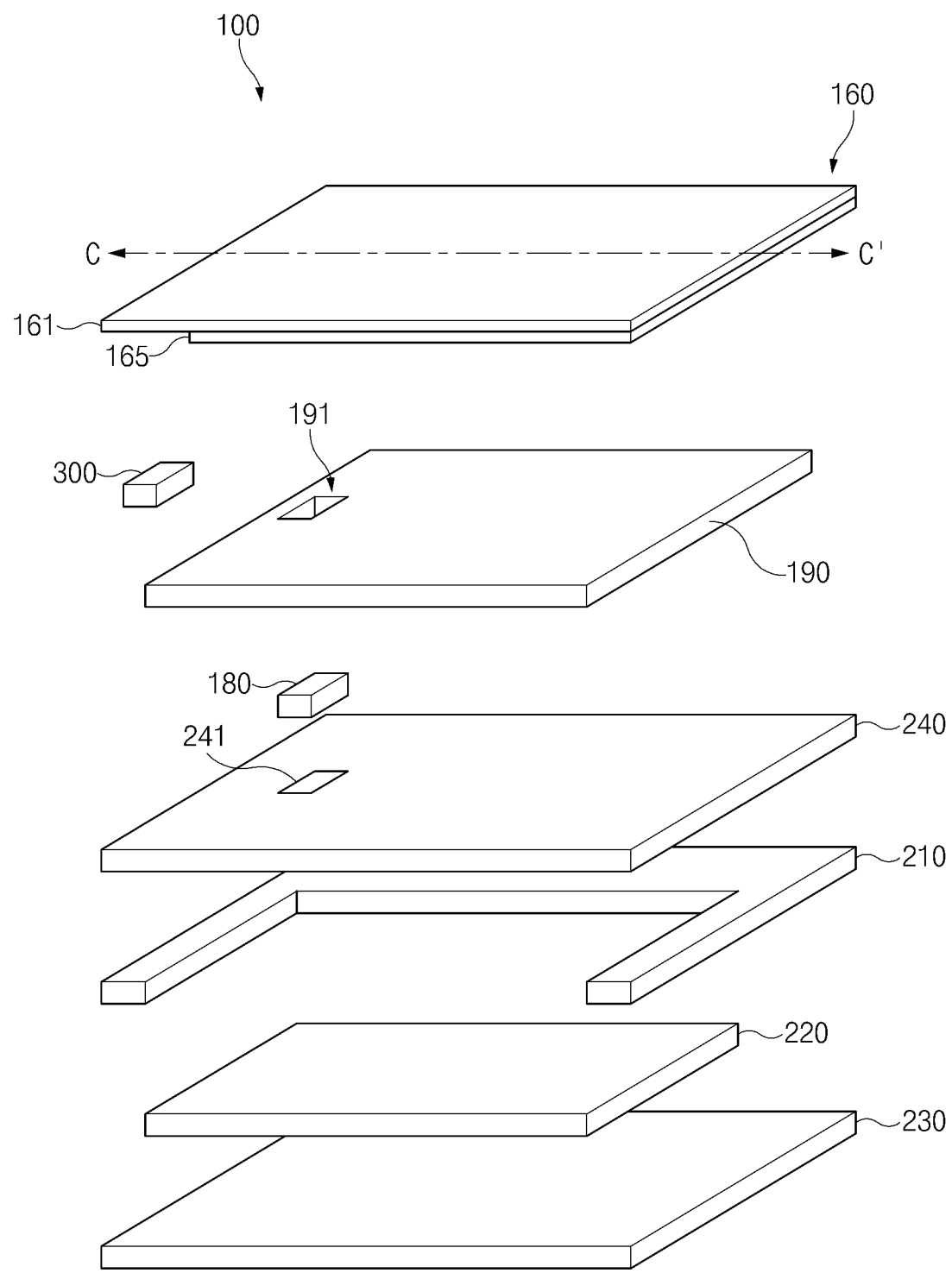
FIG. 3A illustrates an exploded perspective view of an electronic device, according to an embodiment of the present disclosure.

FIG. 3A illustrates an exploded perspective view of an electronic device, according to an embodiment of the present disclosure.

Referring to FIG. 3A, the electronic device 100 includes the display 160, a rear panel 190, the fingerprint sensor 180, a main printed circuit board 210, a battery 220, the light emitting module 300, and a rear cover 230. Additionally, the electronic device 100 may further include a case (or a housing) surrounding a side surface of the display 160. The electronic device 100 may further include a bracket 240, which fixes the display 160, the rear panel 190, the main printed circuit board 210, and the battery 220, between the rear panel 190 and the main printed circuit board 210. The bracket 240 may be provided as a partial configuration of the case (e.g., integrally formed with the case) or may include the case.

As described above, the display 160 includes the window 161 and the display panel 165. The window 161 may have an area larger than a display area of the display panel 165. At least a partial area of the display 160 may be formed to be transparent (or formed to have specific transparency). The display 160 may have the specific transparency (e.g., 5 to 10%) such that light passes through gaps between wiring lines of the display 160. The display 160 may occupy at least part of a front surface of the electronic device 100.

The fingerprint sensor 180 may be disposed under the rear panel 190 located under the display 160, and may be disposed to face a specific area of the display 160 through a sensor arrangement area 191 (e.g., a hole) formed in the rear panel 190. Based on the above-described structure, the fingerprint sensor 180 may sense a fingerprint of a finger touching a specific area of the display 160. According to an embodiment of the present disclosure, since the fingerprint sensor 180 is disposed on a rear surface of the display 160, at least a partial area of which is formed to be transparent through a sensor arrangement area 191, the fingerprint sensor 180 may collect light introduced through the display 160. The fingerprint sensor 180 may receive the light, which is reflected by an object placed in a fingerprint authentication area, from among light totally reflected through the window 161 after being emitted from the light emitting module 300, through the sensor arrangement area 191.

The rear panel 190 may be disposed on a rear surface of the display 160 to protect the display 160 from an impact or to emit heat generated by the display 160. The rear panel 190 may include a protective layer having an embossing pattern, a heat radiating layer, at least part of which is metallic, and the like. According to an embodiment of the present disclosure, the rear panel 190 may include a hole type sensor arrangement area 191, into which the fingerprint sensor 180 is inserted or which is vertically aligned with at least part of the fingerprint sensor 180. The sensor arrangement area 191 may include a hole provided to pass through the front and rear surfaces of the rear panel 190 while having a specific size corresponding to the size of the fingerprint sensor 180.

The bracket 240 may be interposed between the rear panel 190 and the main printed circuit board 210. The bracket 240 includes a sensor seating area 241 in which the fingerprint sensor 180 is seated. The sensor seating area 241 may have a hole shape provided to pass through the front and rear surfaces of the bracket 240 or a recessed shape of a specific depth while having a specific size corresponding to the size of the fingerprint sensor 180. When the sensor seating area 241 has a recessed shape, the bracket 240 may further include a wiring hole or a wiring recess in which wiring lines for electrical connection of the seated fingerprint sensor 180 and the processor disposed on the main printed circuit board 210.

The main printed circuit board 210 may be disposed under the bracket 240. At least one hardware component (e.g., a camera module, a microphone, a speaker, a USB interface, and the like) of the electronic device 100 may be disposed on the main printed circuit board 210. According to an embodiment of the present disclosure, a processor (e.g., at least one of a hardware type of a processor, a processor associated with control of the light emitting module 300, a processor associated with the fingerprint sensor 180, or a processor associated with driving of a display panel) performing processing associated with fingerprint authentication may be disposed on the main printed circuit board 210. In addition, the main printed circuit board 210 may include a contact point electrically connected with the battery 220, and may include a wiring line that is capable of transmitting electric power provided by the battery 220 to the fingerprint sensor 180, the light emitting module 300, and the display 160. The main printed circuit board 210 may be electrically connected with the substrate 185 in which the fingerprint sensor 180 is placed.

The battery 220 may be disposed on a layer that is under the rear panel 190 and parallel to the main printed circuit board 210. The battery 220 may supply electric power to the main printed circuit board 210 electrically connected to the battery 220, and may supply the electric power to components (e.g., the display 160, the fingerprint sensor 180, the light emitting module 300, and the like) under control of the processor of the printed circuit board 210.

The rear cover 230 may be disposed under the main printed circuit board 210 and the battery 220 to at least partially surround the main printed circuit board 210 and the battery 220. The rear cover 230 may be formed of various materials (e.g., plastic, metal, or glass). The rear cover 230 may be fixed to the above-described case or bracket.

The light emitting module 300 may be disposed under one side (e.g., a non-display area as a peripheral area of the display 160) of the display 160. The light emitting module 300 may emit light of a specific wavelength band (e.g., wavelength band of IR or near IR). The light emitting module 300 may be disposed to emit the light from a bottom surface of the window 161 toward the inside of the window 161.

Figure 3B:
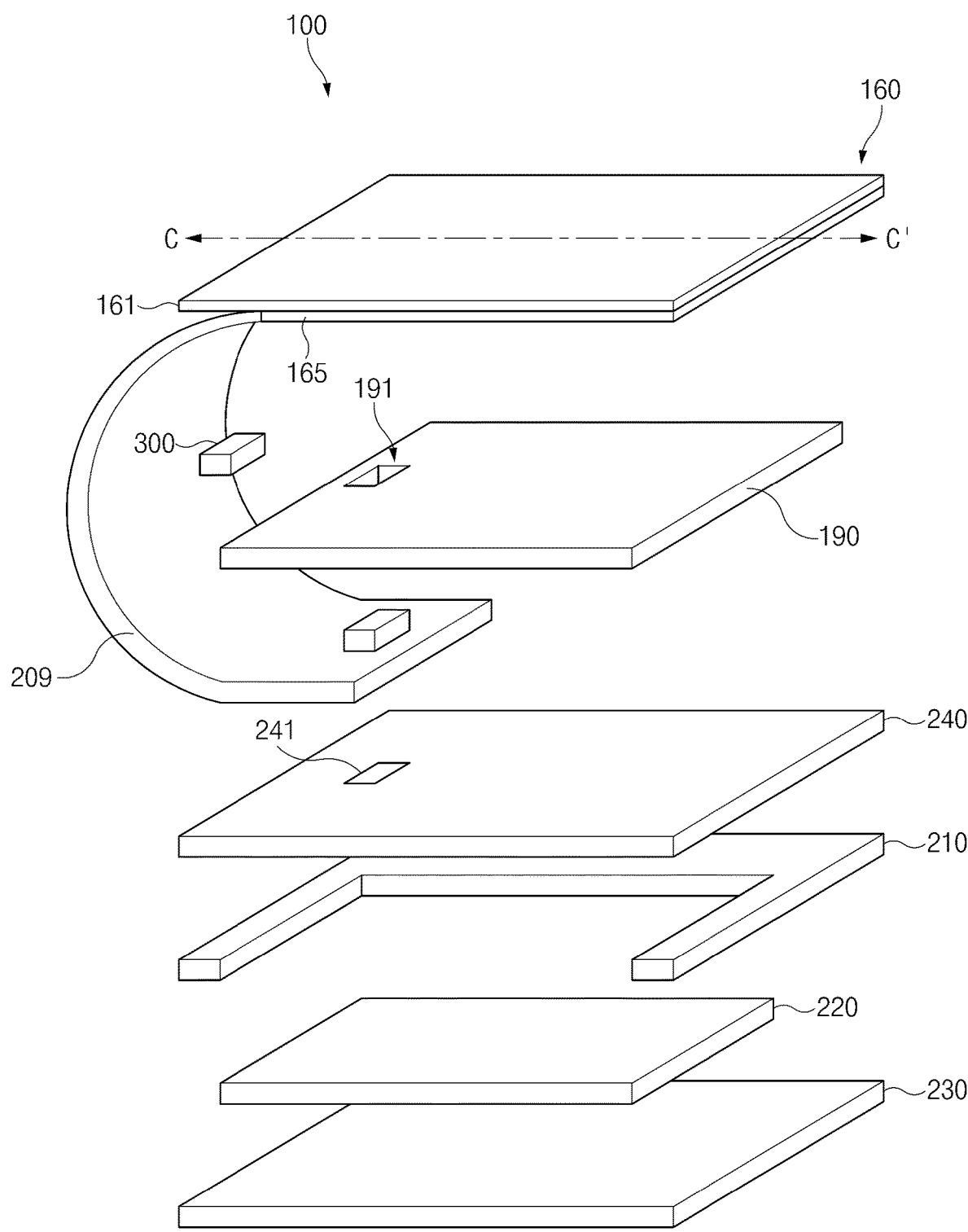
FIG. 3B illustrates an exploded perspective view of an electronic device, according to an embodiment of the present disclosure.

FIG. 3B illustrates an exploded perspective view of an electronic device, according to an embodiment of the present disclosure.

Referring to FIG. 3B, the electronic device 100 includes the display 160, the rear panel 190, the fingerprint sensor 180, the main printed circuit board 210, the battery 220, the light emitting module 300, the display substrate 209, and the rear cover 230. Additionally, the electronic device 100 may further include a case (or a housing) surrounding a side surface of the display 160. The display substrate 209 may be electrically connected with the display panel 165 of the display 160 and may transmit a signal associated with driving of the display panel 165. In this regard, an IC (e.g., a DDI) associated with the driving of the display panel 165 may be mounted on the display substrate 209. In addition, the fingerprint sensor 180 may be disposed on the display substrate 209. Additionally, an IC associated with driving of the fingerprint sensor 180 may be disposed on the display substrate 209. The display substrate 209 is illustrated in FIG. 3B as being interposed between the rear panel 190 and the bracket 240. However, embodiments of the present disclosure are not limited thereto. The display substrate 209 may be disposed under the bracket 240 to be electrically connected with the main printed circuit board 210.

Figure 4A:
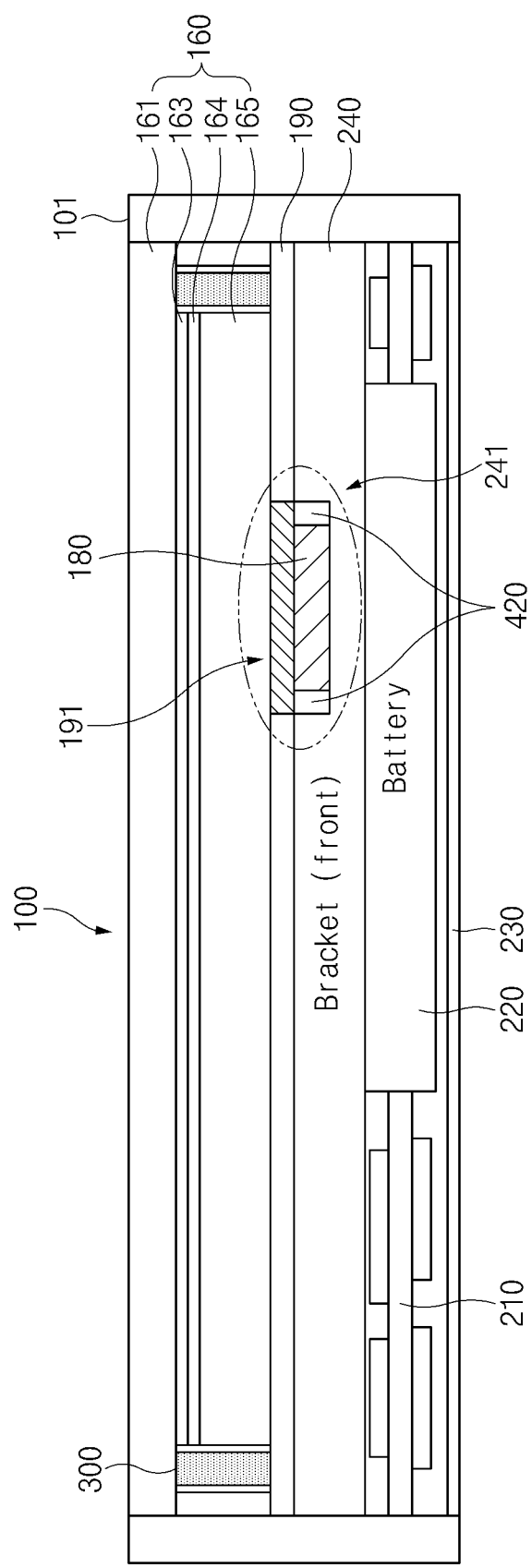
FIG. 4A illustrates an arrangement of a fingerprint sensor of an electronic device, according to an embodiment of the present disclosure.

FIG. 4A illustrates of an arrangement of a fingerprint sensor of an electronic device, according to an embodiment of the present disclosure.

Referring to FIG. 4A, the electronic device 100 includes a case 101, the display 160, the rear panel 190, the fingerprint sensor 180, the light emitting module 300, a display light emitting unit 420, the bracket 240, the main printed circuit board 210, the battery 220, and the rear cover 230.

As described above, the display 160 includes the window 161, the bonding layer 163 (e.g., an OCA), a polarizing layer 164, and the display panel 165. At least part (e.g., a fingerprint authentication area in which the fingerprint sensor 180 is disposed) of the display 160 may be transparent.

The rear panel 190 may be disposed under the display 160 and include a sensor arrangement area 191. The fingerprint sensor 180 may be disposed under the sensor arrangement area 191. The fingerprint sensor 180 may collect, through the sensor arrangement area 191, light passing through the display 160 after being reflected from at least a partial surface of a finger while being emitted from the light emitting module 300 such that the light is totally reflected through the window 161.

The fingerprint sensor 180 may be disposed under the rear panel 190. As illustrated in FIG. 4, the fingerprint sensor 180 may be disposed in the sensor seating area 241 provided on one side of the bracket 240. At least part (e.g., the light receiving unit that may collect light) of a top surface of the fingerprint sensor 180 may be exposed through the sensor arrangement area 191 of the rear panel 190.

The display light emitting unit 420 may include at least one light emitting diode (LED). The display light emitting unit 420 may emit a specific color. Alternatively, the display light emitting unit 420 may emit a plurality of colors. Alternatively, the display light emitting unit 420 may emit light in a specific wavelength band of infrared light in addition to visible light. The display light emitting unit 420 may be disposed adjacent to the fingerprint sensor 180. Alternatively, the display light emitting unit 420 may include a plurality of display light emitting units, and at least one of the plurality of display light emitting units may be disposed around the side of the fingerprint sensor 180. The display light emitting unit 420 may be electrically connected with a processor 120 of the electronic device 100. The display light emitting unit 420 may emit light with a specific color and specific luminance under control of the processor 120. The color or luminance of the display light emitting unit 420 may be adjusted depending on various situations associated with fingerprint sensing.

According to an embodiment of the present disclosure, the display light emitting unit 420 may emit light with the specified luminance or color under the control of the processor with regard to the guiding of the location of the fingerprint sensor 18. In this operation, in the case where the display 160 is turned on, the display light emitting unit 420 may emit light with a first luminance and a first color. In the case where the display 160 is turned off, the display light emitting unit 420 may emit light with a second luminance (e.g., luminance lower than the first luminance) and a second color different from the first color. The display light emitting unit 420 may emit light with a specific wavelength band (e.g., near-infrared light or a wavelength band in the range of 770 to 1100 nm).

According to an embodiment of the present disclosure, if a hovering event or a touch event occurs in an area, in which the fingerprint sensor 180 is disposed, of the display 160, the display light emitting unit 420 may emit light with a third luminance and a third color. The third color may include a color (e.g., violet) that does not interfere with light used for fingerprint sensing of the fingerprint sensor 180. The third luminance may be lower than the second luminance or may be less than a specific magnitude (e.g., 50 nit). Alternatively, the third luminance may have a value of zero (a state where the display light emitting unit 420 is turned off).

According to an embodiment of the present disclosure, the display light emitting unit 420 may emit light with the specific luminance or color based on whether the fingerprint is authenticated. For example, when the fingerprint authentication is successful, the display light emitting unit 420 may emit light with a specific fourth luminance or a fourth color (e.g., yellow, green). For example, when the fingerprint authentication fails, the display light emitting unit 420 may emit light with a specific fifth luminance or a fifth color (e.g., red or black). The fourth color and the fifth color may be differently set depending on a design change of a designer or an area where the meaning of a color is differently interpreted.

According to an embodiment of the present disclosure, the display light emitting unit 420 may emit light with regard to operation of an application associated with the fingerprint sensor 180. If application execution associated with the fingerprint sensing is requested, the display light emitting unit 420 may emit light with the specific luminance or color under control of the processor 120. Alternatively, if a specified gesture (or a user input, for example, a sweep event that sweeps the display 160 in a center direction from a lower portion of a periphery of the electronic device 100) associated with the fingerprint sensing occurs, the display light emitting unit 420 may emit light with the specific luminance or color. Alternatively, the display light emitting unit 420 may guide the location of the fingerprint sensor 180 by emitting light with the specific luminance or color at a specific cycle or in real time.

The bracket 240 is disposed under the rear panel 190 to support the rear panel 190, the display 160, and the like. At least part of the bracket 240 may be formed of a nonmetallic material or at least part of the bracket 240 may be formed of a metallic material. The bracket 240 includes the sensor seating area 241. Additionally, the sensor seating area 241 may include at least one of a wiring recess or a wiring hole, in which the wiring lines of the fingerprint sensor 180 are disposed.

The main printed circuit board 210 may be disposed under the bracket 240, and may be electrically connected to the display 160 and the fingerprint sensor 180. At least one processor related to driving of the display 160 and driving of the fingerprint sensor 180 may be seated on the main printed circuit board 210. The processor may adjust luminance or color of the display light emitting unit 420. The battery 220 may be disposed in a layer that is under the bracket 240 and parallel to the main printed circuit board 210. The rear cover 230 may be disposed to surround the main printed circuit board 210, the battery 220, and the like.

As shown in FIG. 4A, the light emitting module 300 may be disposed in a peripheral area of the display 160. According to an embodiment of the present disclosure, the light emitting module 300 may be disposed under a periphery (e.g., on a horizontal axis or a vertical axis) of the display 160 with respect to the point at which the fingerprint sensor 180 is disposed. While the light emitted from the light emitting module 300 is refracted or reflected (or totally reflected) through the display 160, the light may proceed to the fingerprint sensor 180 after being reflected from the surface of an object (e.g., the finger of a user) that is in contact with the top surface of the display 160.

Figure 4B:
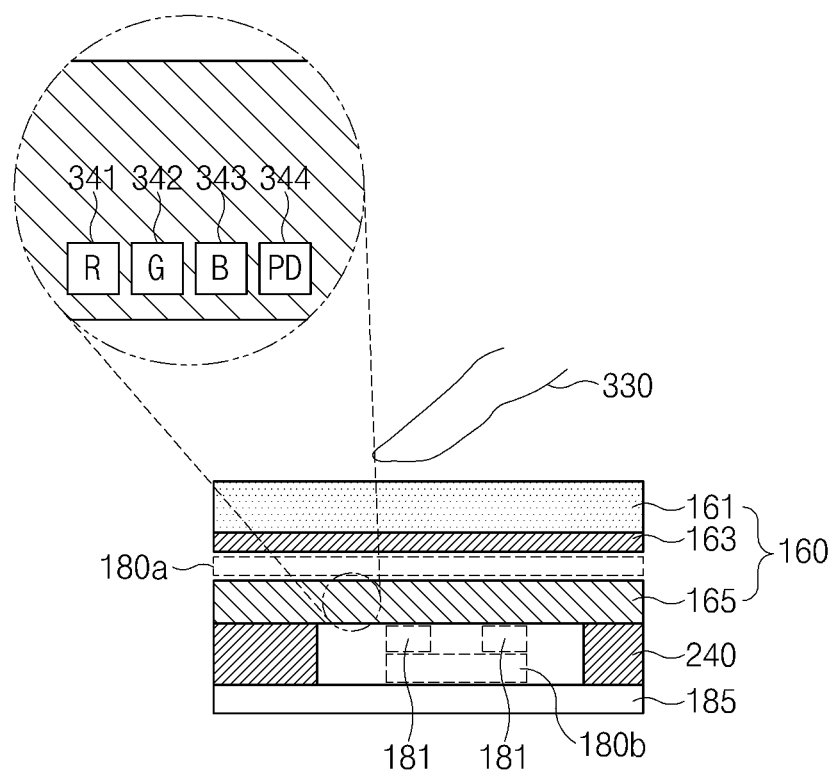
FIG. 4B illustrates a fingerprint sensor area, according to an embodiment of the present disclosure.

FIG. 4B illustrates a fingerprint sensor area, according to an embodiment of the present disclosure.

Referring to FIG. 4B, a structure is illustrated in which a biometric sensor (e.g., a fingerprint sensor 180*a* or a fingerprint sensor 180*b*) sensing biometric information of a user from at least a partial area of the display panel 165 of the electronic device 100 is mounted.

According to an embodiment of the present disclosure, the electronic device 100 includes the window 161, the fingerprint sensor 180*a*, the display panel 165, the fingerprint sensor 180*b*, or the substrate 185. The window 161 may be bonded to the fingerprint sensor 180*a* or the display panel 165 through the bonding layer 163. The electronic device 100 may further include structures 181 for securing a space in which the biometric sensor 180*b* is mounted. In this case, the structures 181 may form at least part of a sealing structure for protecting the fingerprint sensor 180*b*.

According to an embodiment of the present disclosure, the biometric sensor (e.g., the fingerprint sensors 180*a* and 180*b*) may be formed in a partial area (e.g., one area or a plurality of areas) of the display panel 165 or the entire area of the display panel 165.

According to an embodiment of the present disclosure, the biometric sensors 180*a* and 180*b* sensing biometric information may be formed on one surface (e.g., a top surface) (e.g., a separate layer 180*a* on one surface of the display panel 165 or at least a partial area in which pixels 341 to 343 of the display panel 165 are formed) of the display panel 165. The biometric sensor 180*b* may be formed on another surface (e.g., rear surface) of the display panel 165. The biometric sensors 180*a* and 180*b* may include an optical image sensor, an ultrasonic transmission/reception module, or an electrostatic transmission/reception electrode pattern.

According to an embodiment of the present disclosure, the biometric sensor 180*a* may be formed between the bonding layer 163 and the display panel 165 or between the window 161 and the bonding layer 163. The biometric sensor 180*a* may be formed of an electrostatic transmission/reception electrode pattern, and may be formed of a transparent electrode to increase the transmittance of light radiated from the display panel 165. The biometric sensor 180*a* may also include an ultrasonic transmission/reception module.

According to an embodiment of the present disclosure, the biometric sensor 180*b* in the electronic device may be formed on another surface of the display panel 165. An elastic body 181 (e.g., a sponge, a rubber material and the like) for shock absorption between the biometric sensor 180*b* and the display panel 165 or for preventing a foreign object from entering. The fingerprint sensor 180*b* may include an image sensor. The image sensor may radiate light (e.g., visible light, infrared light, or ultraviolet light) emitted from a light source (e.g., the display panel 165 or an IR LED) to the fingerprint of a user, and may detect the light reflected from the fingerprint of the user by using the image sensor.

Figure 5A:
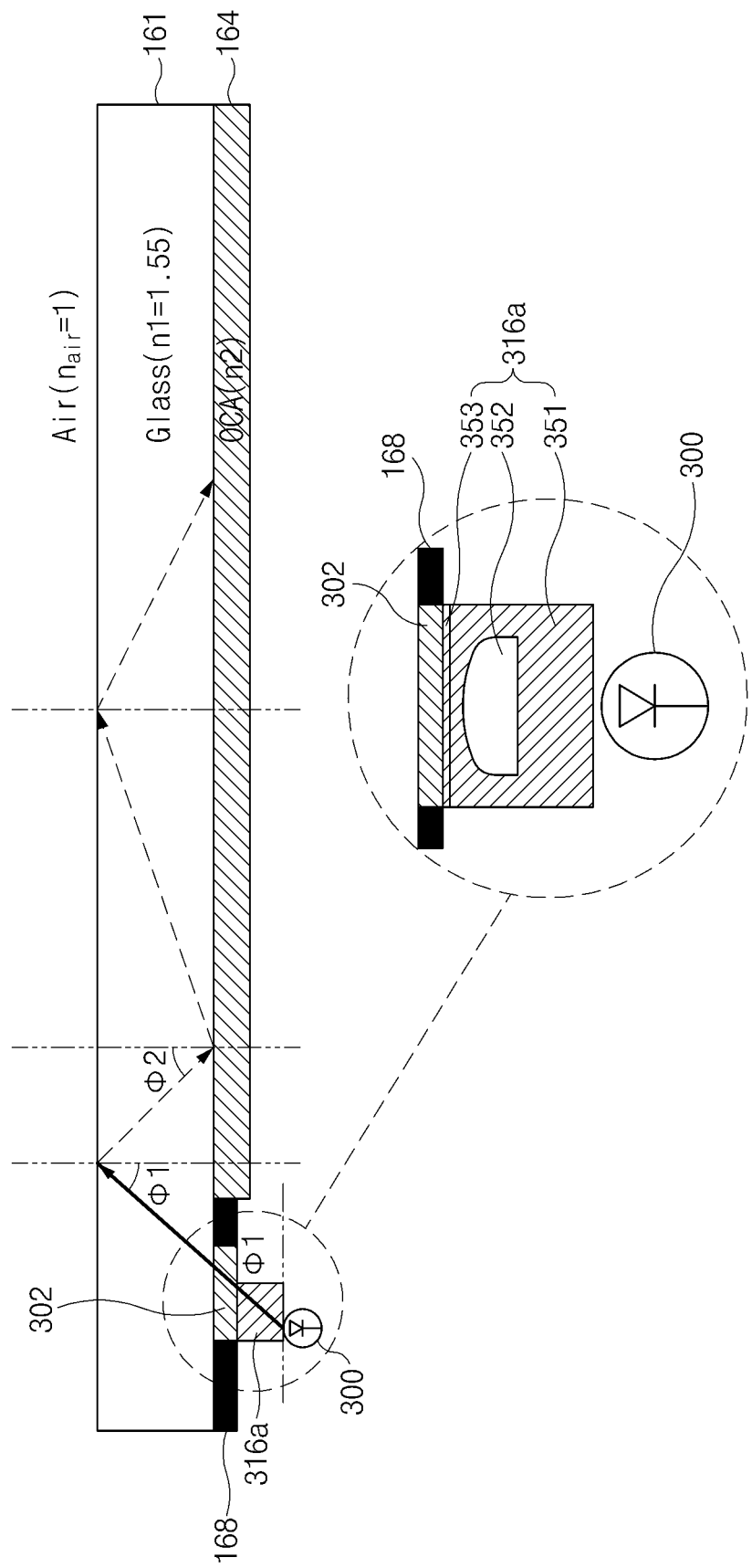
FIG. 5A illustrates a configuration of components associated with fingerprint sensing in an electronic device, according to an embodiment of the present disclosure.

FIG. 5A illustrates a configuration of components associated with fingerprint sensing in an electronic device, according to an embodiment of the present disclosure.

Referring to FIG. 5A, a part of a configuration of the electronic device 100 includes the window 161, the bonding layer 163, a printed layer 168, a light transmitting layer 302, the light emitting module 300, and a first light guide member 316*a*. The light transmitting layer 302 may be provided in a hole shape in which the printed layer 168 is removed. In the case where the light transmitting layer 302 is provided in a hole shape, the first light guide member 316*a* may directly face the bottom surface of the window 161 while being disposed in the hole.

As described above, the window 161 may be formed of a transparent material (e.g., glass, transparent plastic, and the like). A refractive index of the window 161 may be greater than that of an air layer and the bonding layer 163. The window 161 may have a refractive index in the range of 1.5 to 1.6.

The bonding layer 163 may be disposed under the window 161 and may fix the window 161 and display panel. The bonding layer 163 may include a light-permeable adhesive material. The bonding layer 163 may have the refractive index in the range of 1.3 to 1.47 (for example, 1.4) which is relatively lower than the refractive index of the window 161.

The printed layer 168 may include a layer on which a specific pattern associated with the appearance of the electronic device 100 is printed. The printed layer 168 may be formed of a material having a relatively low light transmittance.

The light transmitting layer 302 may be formed in at least a partial area of the printed layer 168. The light transmitting layer 302 may have specific transparency at which the light that is transmitted through the first light guide member 316*a* after being emitted from the light emitting module 300 is incident on the window 161. According to an embodiment of the present disclosure, the light transmitting layer 302 may have a degree of transparency or a material where an IR signal (or a signal of a wavelength band that is capable of being used for fingerprint sensing, such as an NIR wavelength band) is transmitted. The first light guide member 316*a* may be disposed under the light transmitting layer 302.

The first light guide member 316*a* may transmit the light emitted by the light emitting module 300 to the window 161 through the light transmitting layer 302. In this process, the first light guide member 316*a* may allow the light to be incident toward the inside of the window 161 while having a specific inclination from the bottom surface of the window 161, by changing a path of the light emitted by the light emitting module 300. The first light guide member 316*a* may be formed of a material having a refractive index which is the same as the refractive index of the window 161 or a refractive index which is relatively higher than the refractive index of the window 161. As such, the light transmitted through the first light guide member 316a may proceed to the inside of the window 161 while being refracted to have a specific inclination without being totally reflected from the bottom surface of the window 161. The first light guide member 316a includes a first body part 351, a first lens part 352, and an adhesive part 353.

The first body part 351 may be formed in a rectangular or polyhedral shape. The first lens part 352 may be disposed inside the first body part 351. The adhesive part 353 may be disposed at one end of the first body part 351 and may be fixed to one surface (e.g., one side of a bottom surface) of the window 161.

The first lens part 352 may be formed inside the first body part 351. At least part of the first lens part 352 may include a convex shape in a direction in which the window 161 faces the bottom surface of the window 161 from an area under the window 161. As such, the first lens part 352 may allow the light to be incident while having a specific inclination from the bottom surface of the window 161 by changing the path of the light emitted by the light emitting module 300.

The adhesive part 353 may fix the first light guide member 316a to the bottom surface of the light transmitting layer 302. The adhesive part 353 may have specific transparency such that the light of a specific wavelength band transmitted through the first light guide member 316a enters the window 161 through the light transmitting layer 302. The adhesive part 353 may include an OCA tape.

The light emitting module 300 may be disposed under the first light guide member 316a to emit light to the first light guide member 316a. The inclination of the light emitted from the light emitting module 300 proceeding via the first light guide member 316a may be changed. As such, the light proceeding via the first light guide member 316a after being emitted by the light emitting module 300 may proceed to the inside of the window 161 while having a specific inclination from the bottom surface of the window 161.

Figure 5B:
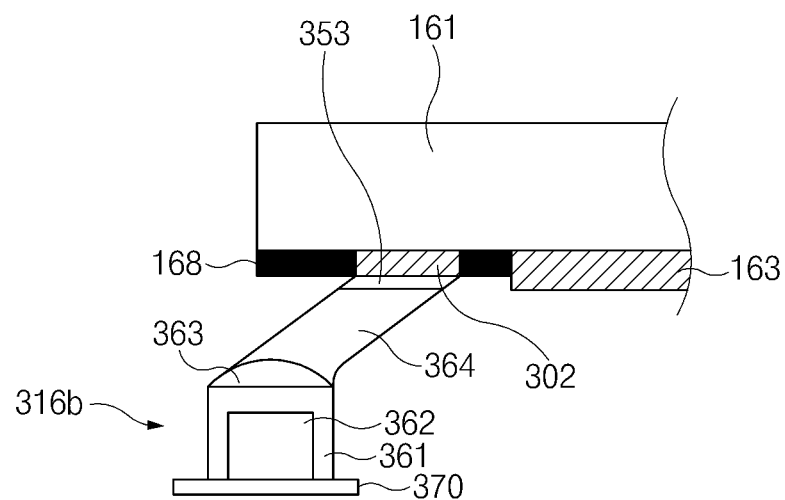
FIG. 5B illustrates a configuration associated with fingerprint sensing, according to an embodiment of the present disclosure.

According to an embodiment of the present disclosure, in the case where the light emitted from the light emitting module 300 is reflected between the window 161 and an air layer at an angle θ2 after being incident at an angle θ1, if the refractive index of the air layer is 1, the refractive index of the window 161 is 1.55, and the refractive index of the bonding layer 163 is 1.4, the angle θ1 and the angle θ2 may be calculated through Equation (1).

$$\theta_2 \geq \sin^{-1}\frac{n2}{n1} = \sin^{-1}\frac{1.4}{1.55} \approx \geq 64.59 \text{ degree}, \theta_1 \leq 25 \text{ degree}, \quad (1)$$

$$\text{Incident angle}_{glass-air} = \sin^{-1}\frac{n_{air}}{n1} = \sin^{-1}\frac{1}{1.55} \approx \geq 40.18 \text{ degree},$$

therefore, $\theta_2 \geq 64.59$ degree seems to be sufficient to make TIR in glass FIG. 5B illustrates a configuration of components associated with fingerprint sensing, according to another embodiment of the present disclosure.

Referring to FIG. 5B, the electronic device 100 includes the window 161, the printed layer 168, the light transmitting layer 302, the bonding layer 163, and a second light guide member 316b. The window 161, the printed layer 168, the light transmitting layer 302, and the bonding layer 163 may include a configuration substantially the same as or similar to components described in FIG. 5A above.

The second light guide member 316b includes a sensor substrate 370, a light emitting module 362, a light emitting body part 361, a second lens part 363, a lens body part 364, and the adhesive part 353.

The light emitting module 362 may be seated in the sensor substrate 370. The sensor substrate 370 may be at least part of the above-described substrate 185. The sensor substrate 370 may include at least one signal line for supplying electric power to the light emitting module 362. The sensor substrate 370 in which the light emitting module 362 is mounted may be fixed to one side (e.g., a part disposed under a periphery of the window 161 in the bracket 240) of the electronic device 100.

The light emitting module 362 may emit light of a specific wavelength band by using the electric power supplied through the sensor substrate 370. The light emitting module 362 may emit light of an infrared wavelength band or a wavelength band close to infrared light (e.g., 780 nm to 1100 nm). The light emitted from the light emitting module 362 may proceed to the second lens part 363.

The light emitting body part 361 may include a structure surrounding the light emitting module 362. The light emitting body part 361 may be formed of transparent epoxy, transparent plastic, and the like. While surrounding the light emitting module 362, one side of the light emitting body part 361 may be mounted on the sensor substrate 370. At least one surface of the light emitting body part 361 may face a bottom surface of the second lens part 363.

The second lens part 363 may be inclined at a specific angle with respect to a horizontal surface (e.g., the bottom surface of the window 161) such that the light emitted from the light emitting module 362 is incident from the bottom surface of the window 161 at a specific angle. The convex part of the second lens part 363 may be disposed to be inclined to the right with respect to a direction perpendicular to the bottom surface of the window 161. As such, the light emitted from the light emitting module 362 may be focused while passing through the second lens part 363 and may proceed to the lens body part 364 while having a specific inclination.

The lens body part 364 may transmit the light propagated from the second lens part 363 to a specific area under the window 161. In this regard, the lens body part 364 may be provided in a cylindrical form (or a column form of which the internal space is filled or empty) inclined at a specific angle. According to an embodiment of the present disclosure, the lens body part 364 may be formed such that the area of the cross section gradually increases as it goes from the area of the second lens part 363 to the window 161. As such, the light focused by the second lens part 363 may be incident on the window 161 with a specific inclination while spreading through the lens body part 364.

According to an embodiment of the present disclosure, the shape of the second lens part 363 may be provided on a surface facing a specific part (e.g., the light emitting body 361) of the lens body 364. The shape of the second lens part 363 may be formed by recessing one end (e.g., one end facing the light emitting body part 361) of the lens body part 364 inwardly. In this case, the second lens part 363 may be integrated with the lens body part 364.

The adhesive part 353 may be disposed in the other end of the lens body part 364. The adhesive part 353 may fix the lens body part 364 to one side of a bottom surface of the window 161. The adhesive part 353 may include a configuration substantially the same as or similar to the above-described adhesive part.

Figure 5C:
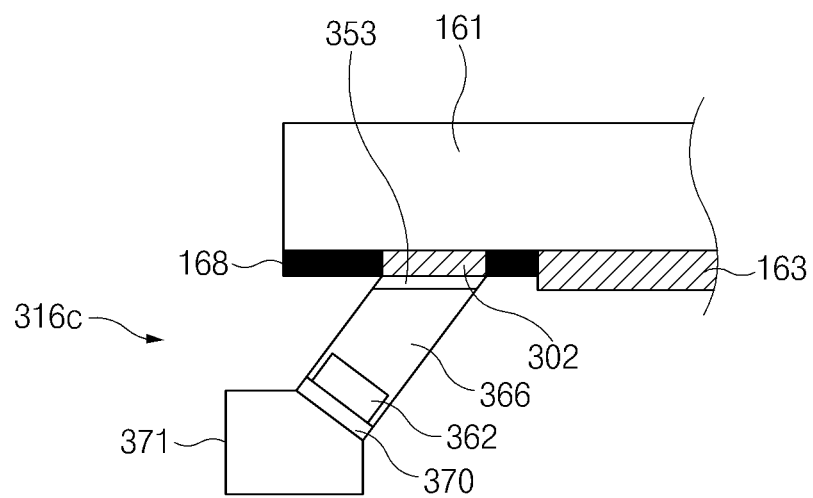
FIG. 5C illustrates a configuration associated with fingerprint sensing, according to an embodiment of the present disclosure.

FIG. 5C illustrates a configuration of components associated with fingerprint sensing, according to an embodiment of the present disclosure.

Referring to FIG. 5C, the electronic device 100 includes the window 161, the printed layer 168, the bonding layer 163, a third light guide member 316c, and the light transmitting layer 302. The window 161, the printed layer 168, the light transmitting layer 302, and the bonding layer 163 may include a configuration substantially the same as components described in FIG. 5A above.

The third light guide member 316c includes a fixing part 371, the sensor substrate 370, the light emitting module 362, a second body part 366, and the adhesive part 353.

The fixing part 371 may include one surface capable of being fixed to a component (e.g., the bracket 240 and the like) of the electronic device 100 and another surface in which the sensor substrate 370 is seated with a specific inclination. The fixing part 371 may be shaped as a polyhedron. One surface of the fixing part 371 in which the sensor substrate 370 is seated may be provided in a direction in which the light of the light emitting module 362 disposed on the sensor substrate 370 is transmitted to one side of a bottom surface of the window 161. The sensor substrate 370 may be fixed to one surface of the fixing part 371.

The sensor substrate 370 may be seated and fixed on one surface of the fixing part 371. The light emitting module 362 may be seated in the sensor substrate 370. The fixing part 371 and the sensor substrate 370 may be at least part of the above-described substrate 185. The sensor substrate 370 may include at least one signal line for supplying electric power to the light emitting module 362.

The light emitting module 362 may emit light of a specific wavelength band based on the electric power supplied through the sensor substrate 370. The light emitting module 362 may emit light of an infrared wavelength band or a wavelength band close to infrared light (e.g., 780 nm to 1100 nm). The light emitted from the light emitting module 362 may be transmitted to the bottom surface of the window 161 through the second body part 366. If the sensor substrate 370 is inclined, the light emitting module 362 may be disposed with a specific inclination. As such, the light emitted from the light emitting module 362 may be emitted with a specific inclination with respect to the horizontal surface of the window 161.

A second body part 366 may include a structure surrounding the light emitting module 362. The second body part 366 may be formed of transparent epoxy or transparent plastic. While surrounding the light emitting module 362, one side of the second body part 366 may be mounted on the sensor substrate 370. The second body part 366 may be disposed with a specific inclination with respect to a bottom surface of the window 161 such that the second body part 366 corresponds to the inclined sensor substrate 370. One surface of the second body part 366 may be disposed to face the bottom surface of the window 161. The second body part 366 may have a specific cross section (e.g., a circular cross section, an elliptical cross section, or a polygonal cross section). According to an embodiment of the present disclosure, the second body part 366 may be formed such that sizes and shapes of a cross section of an area adjacent to the light emitting module 362 and a cross section of an area adjacent to the window 161 are different from each other. For example, similar to the first body part 364, as being adjacent to the window 161, the area of the cross section of the second body part 366 may gradually increase.

Since the adhesive part 353 is interposed between one surface, which faces the window 161, of the second body part 366 and one bottom surface of the window 161, the second body part 366 may be fixed to one side of the bottom surface of the window 161. The adhesive part 353 may include a configuration substantially the same as or similar to the above-described adhesive part.

Figure 6:
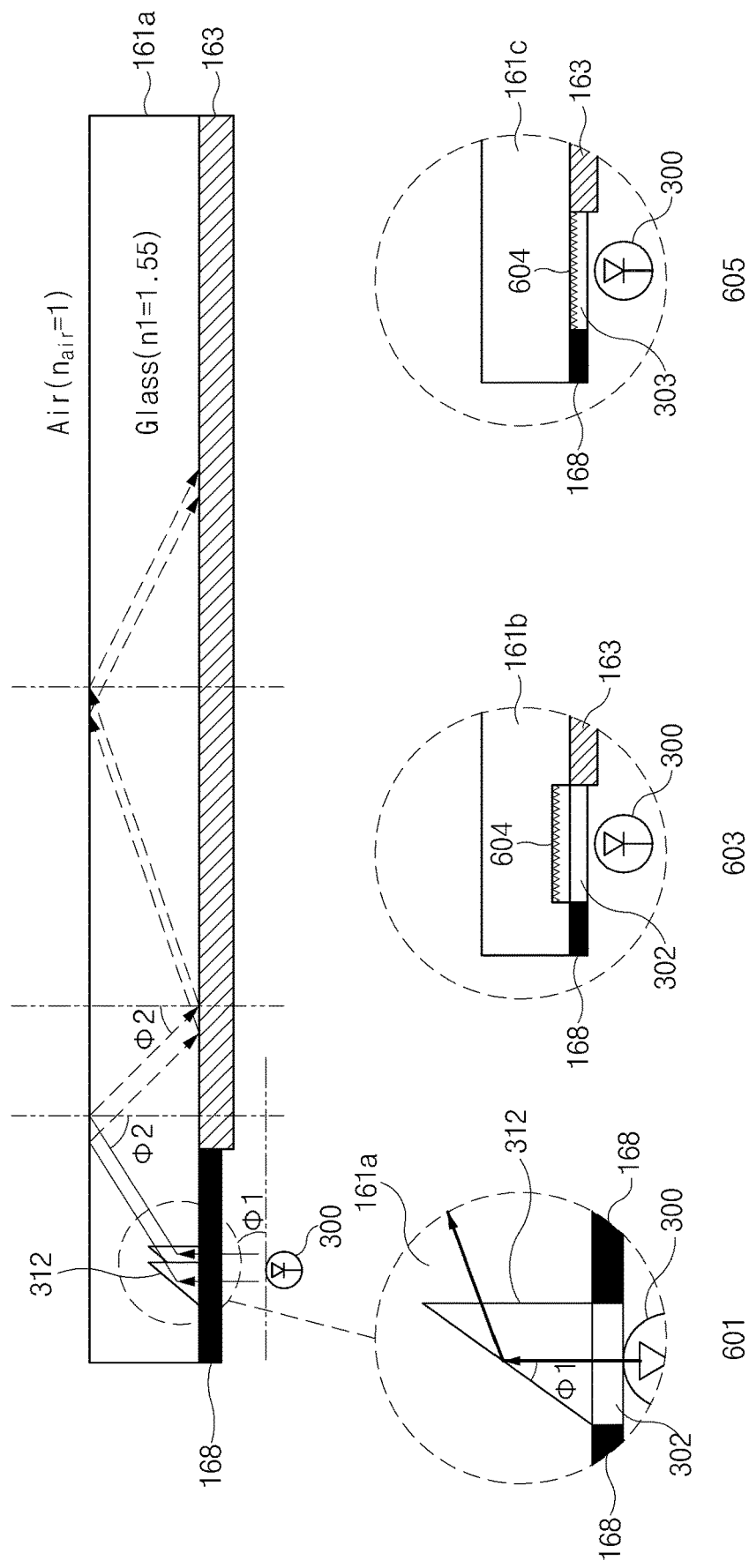
FIG. 6 illustrates a configuration of a window of an electronic device, according to an embodiment of the present disclosure.

FIG. 6 illustrates a configuration of a window of an electronic device, according to an embodiment of the present disclosure.

Referring to an image 601 in FIG. 6, for example, a part of a configuration of the electronic device 100 includes a first window 161a, the bonding layer 163, the printed layer 168, the light transmitting layer 302, and the light emitting module 300. The bonding layer 163 and the printed layer 168 may include a configuration substantially the same as or similar to above-described components.

The bonding layer 163 may be disposed in a first area under the first window 161a, and the light emitting module 300 may be disposed in a second area under the first window 161a. An optical pattern 312 (or a refraction part or a light change layer) may be formed in the first window 161a corresponding to the second area in which the light emitting module 300 is disposed. The optical pattern 312 may be formed on one side of a lower portion of a periphery of the first window 161a by laser processing and the like. The optical pattern 312 may have an inclination angle of a specific magnitude such that the light emitted from the light emitting module 300 disposed under the first window 161a proceeds in a specific direction (e.g., a direction in which the fingerprint sensor 180 is disposed). In addition, since the optical pattern 312 is provided to have a specific first angle (e.g., $\theta1$) with respect to the light emitted from the light emitting module 300, the light proceeding to the inside of the window 161 after being reflected from the optical pattern 312 may be totally reflected inside the first window 161a.

The light emitting module 300 may be disposed to face the light transmitting layer 302 and may emit light to an area, in which the optical pattern 312 is formed, of the first window 161a, through the light transmitting layer 302. Alternatively, in the case where the light transmitting layer 302 is provided in a hole shape, the light emitting module 300 may be disposed to directly face the bottom surface of the first window 161a.

Referring to an image 603 in FIG. 6, a part of a configuration of the electronic device 100 includes a second window 161b, the bonding layer 163, the printed layer 168, the light transmitting layer 302, and the light emitting module 300. The bonding layer 163 and the printed layer 168 may include a configuration substantially the same as or similar to above-described components.

The bonding layer 163 may be disposed in a first area under the second window 161b, and the light emitting module 300 may be disposed in a second area under the second window 161b. A recess of a specific size may be formed in the second window 161b corresponding to the second area in which the light emitting module 300 is disposed. An optical member 604 may be disposed in the recess of the specific size. The optical member 604 may include a specific pattern such that the light emitted from the light emitting module 300 disposed under the second window 161b proceeds (e.g., is totally reflected) in a specific direction (e.g., direction in which the fingerprint sensor 180 is disposed). The pattern of the optical member 604 may be provided the same as or similar to a scratch pattern described in the image 601.

The light transmitting layer 302 may include the recess provided in the second window 161*b*, and the size of the recess may correspond to the optical member 604 that is disposed in the recess. The light emitting module 300 may be disposed under the light transmitting layer 302. In the case where the light transmitting layer 302 is provided in a hole shape formed by removing the printed layer 168, the light emitting module 300 may be disposed to directly face the optical member 604.

The light emitting module 300 may emit light of a specific wavelength band to the optical member 604 via the light transmitting layer 302. Alternatively, the light emitting module 300 may directly face the optical member 604 and may emit light to the optical member 604. An angle at which the light emitted from the light emitting module 300 proceeds after passing through the optical member 604 may be changed. In this case, the light may proceed while being totally reflected inside the second window 161*b*.

Referring to an image 605 in FIG. 6, a part of a configuration of the electronic device 100 includes a third window 161*c*, the bonding layer 163, the printed layer 168, an optical member 303, and the light emitting module 300. The bonding layer 163 and the printed layer 168 may include a configuration substantially the same as or similar to above-described components.

The bonding layer 163 may be disposed in a first area under the third window 161*c*, and the optical member 303 may be disposed in at least one second area under the third window 161*c*. The light emitting module 300 may be disposed under the optical member 303. The optical member 303 may allow the light emitted from the light emitting module 300 to proceed to the third window 161*c* and may allow the light to be totally reflected inside the third window 161*c* by changing the propagation direction. At least part of a pattern included in the optical member 303 may include the shape of the above-described optical pattern 312. Alternatively, the optical member 303 may include various shapes such as a polygonal pattern, a hemispherical pattern, a semi-cylindrical pattern and the like as well as a triangular pattern. The optical member 303 may be provided such that a prism sheet is disposed on the light transmitting layer 302. Alternatively, the light transmitting layer 302 may be provided in the form including the prism pattern.

Figure 7:
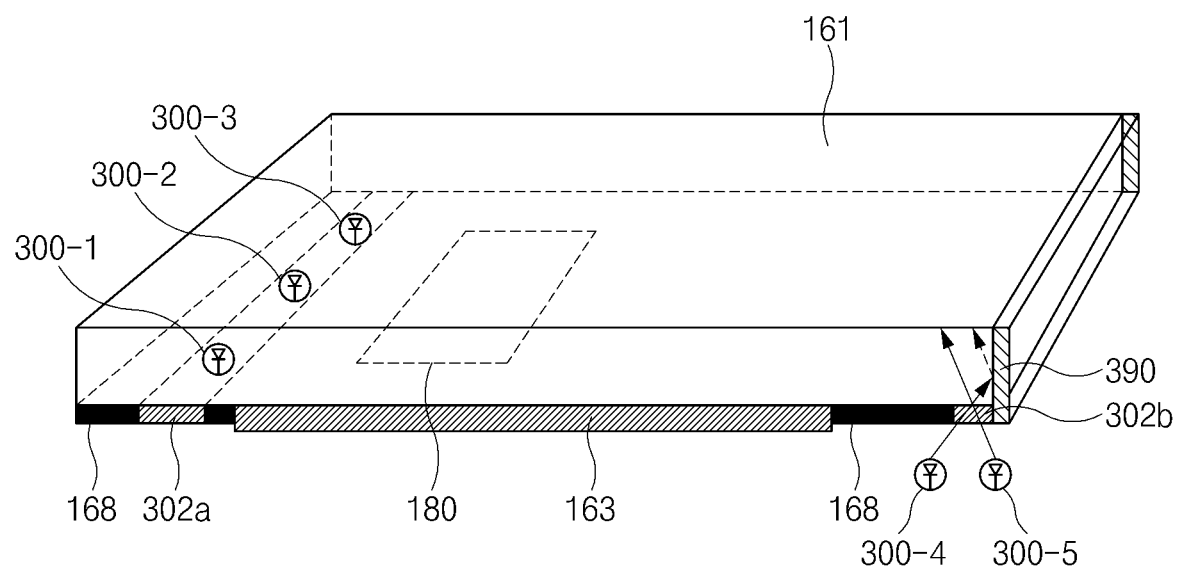
FIG. 7 illustrates an electronic device including a plurality of light emitting modules, according to an embodiment of the present disclosure.

FIG. 7 illustrates an electronic device including a plurality of light emitting modules, according to an embodiment of the present disclosure.

Referring to FIG. 7, the electronic device 100 includes the window 161, the fingerprint sensor 180, the bonding layer 163, the printed layer 168, the light transmitting layers 302*a* and 302*b*, a reflection plate 390, and a plurality of light emitting modules 300_1, 300_2, 300_3, 300_4, and 300_5.

As described above, the window 161 may be formed of a material (e.g., glass) having a specific surface and thickness. The bonding layer 163 may be disposed in a first area under the window 161. At least one of the printed layer 168 or the light transmitting layers 302*a* and 302*b* may be disposed in a second area (e.g., left and right peripheral areas with respect to the first area) under the window 161. According to an embodiment of the present disclosure, in the second area, the first light transmitting layer 302*a* and the second light transmitting layer 302*b* may be disposed in left and right peripheries under the window 161, respectively.

The light transmitting layers 302*a* and 302*b* may be formed in a first direction (e.g., a width or longitudinal direction) of the window 161 with a specific area. The light transmitting layers 302*a* and 302*b* may be provided in the form of a rail having a specific length. The light transmitting layers 302*a* and 302*b* may be disposed adjacent to the printed layer 168 or may be interposed between a plurality of the printed layers 168. A part of light emitting modules 300_1, 300_2, and 300_3 of the light emitting modules 300_1, 300_2, 300_3, 300_4, and 300_5 may be disposed under the light transmitting layers 302*a* and 302*b*. The light transmitting layers 302*a* and 302*b* are illustrated in FIG. 7 as being formed in a rail shape. However, embodiments of the present disclosure are not limited thereto. The light transmitting layers 302*a* and 302*b* may be provided in a lattice shape of a specific size corresponding to each of areas in which the part of light emitting modules (e.g., 300_1, 300_2, and 300_3) are disposed. The printed layer 168 may be disposed in a periphery of each of the lattice-shaped light transmitting layers 302*a* and 302*b*.

The light emitting modules (e.g., 300_1, 300_2, and 300_3) disposed in the first light transmitting layer 302*a* may be disposed at a specific interval. The interval of the light emitting modules 300_1, 300_2, and 300_3 may vary according to the size and location of the fingerprint sensor 180. The light emitting modules 300_1, 300_2, and 300_3 may be disposed at a specific interval within the width of the fingerprint sensor 180. As described above, a light change layer (e.g., the optical member 303 or the optical member 604) may be disposed in the first light transmitting layer 302*a*. Alternatively, the above-mentioned light change layer (e.g., the optical pattern 312) may be disposed in a specific area under the window 161 corresponding to the first light transmitting layer 302*a*. As such, the light emitted from light emitting modules 300_1, 300_2, and 300_3 may be incident on the window 161 with a specific inclination while passing through the first light transmitting layer 302*a*, and may proceed to the fingerprint sensor 180 while being totally reflected inside the window 161. According to an embodiment of the present disclosure, the electronic device 100 may further include the above-described light guide member disposed adjacent to the light emitting modules 300_1, 300_2, and 300_3.

The second light transmitting layer 302*b* may be disposed adjacent to an area in which the reflection plate 390 is disposed. The second light transmitting layer 302*b* may be formed of a material capable of transmitting light of a specific wavelength band emitted from the light emitting modules 300_4 and 300_5. The above-described light change layer may be disposed in the second light transmitting layer 302*b*. Alternatively, a light change layer (e.g., the optical pattern 312) may be disposed in a specific area under the window 161 corresponding to the second light transmitting layer 302*b*.

The reflection plate 390 may be disposed on a side surface of the window 161. The reflection plate 390 may allow the light to proceed in the propagation direction of the window 161 by changing the propagation direction of the light emitted from the light emitting module (e.g., the first light emitting module 300_4) disposed under the window 161. The reflection plate 390 may include at least one of a metal material or a non-metal material, and may be disposed such that incident light proceeds to the inside of the window 161 while the direction of incident light has a specific angle. The light emitted from the first light emitting module 300_4 may proceed to the reflection plate 390 through the second light transmitting layer 302*b*, and may proceed to the inside of the window 161 while the propagation direction is changed by the reflection plate 390. The electronic device 100 may further include a light guide member interposed between the first light emitting module 300_4 and the window 161. The light guide member may allow the light emitted from the first light emitting module 300_4 to proceed in the direction of the reflection plate 390.

The second light emitting module 300_5 may emit light of a specific wavelength band toward the inside of the window 161 through the second light transmitting layer 302b. The light guide member may be interposed between the second light emitting module 300_5 and the second light transmitting layer 302b. The light guide member associated with the second light emitting module 300_5 may allow the light emitted from the second light emitting module 300_5 to proceed to the inside of the window 161.

As described above, according to an embodiment of the present disclosure, the electronic device 100 includes at least one of a plurality of light emitting modules 300_1, 300_2, 300_3, 300_4, and 300_5. The light emitted from light emitting modules 300_1, 300_2, 300_3, 300_4, and 300_5 may proceed while being totally reflected inside the window 161.

Figure 8:
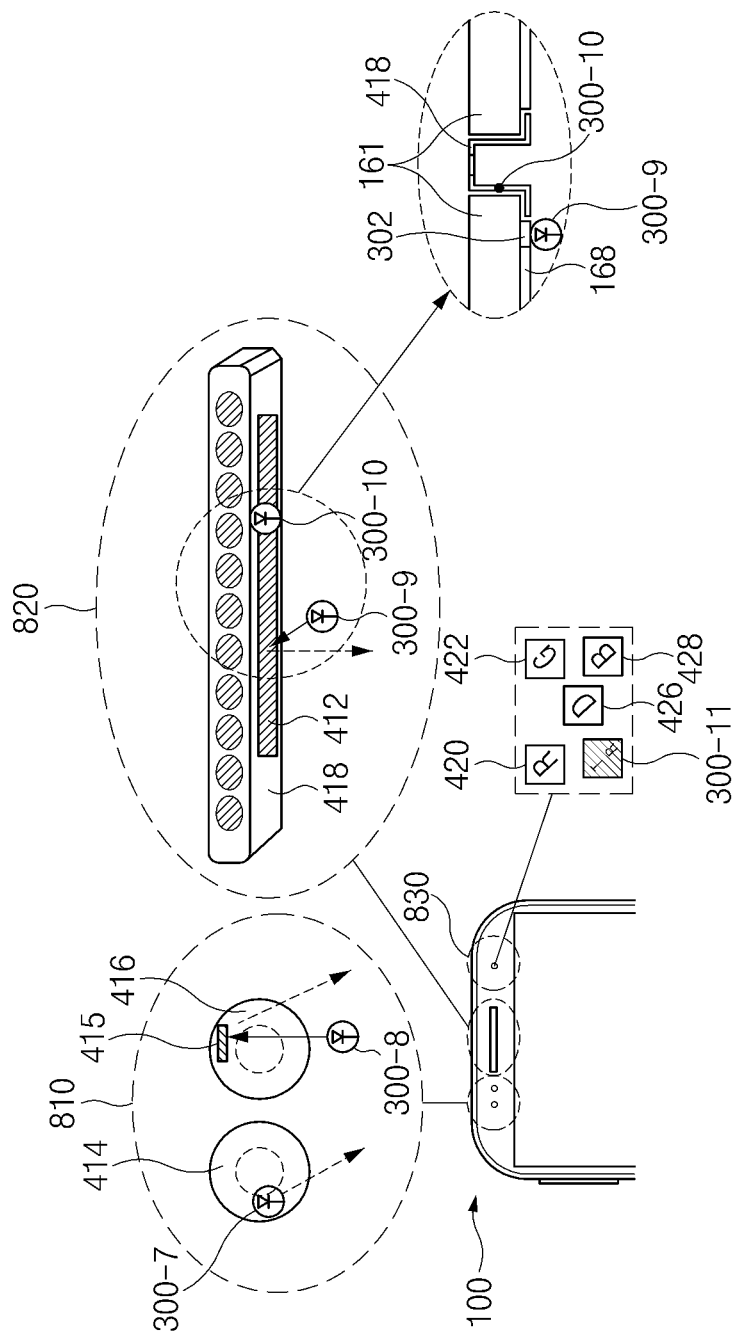
FIG. 8 illustrates various arrangement forms of a plurality of light emitting modules, according to an embodiment of the present disclosure.

FIG. 8 illustrates various arrangement forms of a light emitting module, according to an embodiment of the present disclosure.

Referring to FIG. 8, the electronic device 100 includes a proximity sensor 810, a speaker housing 820 (or a receiver), and an illuminance sensor 830.

According to an embodiment of the present disclosure, the electronic device 100 includes light emitting modules 300_7 and 300_8 disposed in the proximity sensor 810. The third light emitting module 300_7 may be disposed in a light emitting unit 414 (or a light receiving unit) of the proximity sensor 810. The third light emitting module 300_7 may be disposed under the light emitting unit 414 and may emit light of a specific wavelength band to the window 161 through a specific area of the light emitting unit 414. The fourth light emitting module 300_8 and a reflection member 415 may be disposed in the light receiving unit 416 (or a light emitting unit) of the proximity sensor 810. The fourth light emitting module 300_8 may emit light to a specific area of the light receiving unit 416. The fourth light emitting module 300_8 may emit light to the reflection member 415 disposed in the light receiving unit 416, and the light reflected by the reflection member 415 may proceed to the inside of the window 161.

According to an embodiment of the present disclosure, a fifth light emitting module 300_9 may be disposed in an area (e.g., a specific area under the window 161) adjacent to an area in which the speaker housing 820 is disposed, and a reflection area 412 may be disposed on a side wall of the speaker housing 820. As such, light of the specific wavelength band emitted from the fifth light emitting module 300_9 may proceed to the reflection area 412, and the light reflected by the reflection area 412 may proceed to the inside of the window 161.

According to an embodiment of the present disclosure, a hole or a recess may be provided on one side of the speaker housing 820, and a sixth light emitting module 300_10 may be disposed in the hole or recess. The sixth light emitting module 300_10 may emit light of the specific wavelength band from one side of the window 161 facing the side wall of the speaker housing 820. As such, the light emitted from the sixth light emitting module 300_10 may directly proceed to the inside of the window 161. In this case, the sixth light emitting module 300_10 may emit light toward the inside of the window 161 with a specific inclination such that the light is totally reflected inside the window 161.

According to an embodiment of the present disclosure, a seventh light emitting module 300_11 may be disposed in an area adjacent to the illuminance sensor 830 or together with light pixels 420, 422, 426, and 428 of the illuminance sensor 830. The seventh light emitting module 300_11 may emit light of the specific wavelength band to the window 161. Herein, the seventh light emitting module 300_11 may emit light with a specific inclination such that the light is totally reflected toward the inside of the window 161 from an area in which the illuminance sensor 830 is disposed.

According to an embodiment of the present disclosure, the light emitting module may be mounted in an edge part of the electronic device in which at least a partial periphery is curved or under a periphery of a window so that the light emitting module may be mounted on the same layer as the display panel. Alternatively, the light emitting module may be mounted in at least part of a pixel area of the display panel.

According to an embodiment of the present disclosure, an electronic device includes a display panel through which light of a specific wavelength band passes through at least a part of the display panel, a window disposed on the upper side of the display panel, a light emitting module disposed under a peripheral area of the window, and a fingerprint sensor disposed under one side of the display panel and sensing the light passing through the display panel due to the reflection of an object disposed on the window while being totally reflected inside the window after being emitted from the light emitting module.

According to an embodiment of the present disclosure, the light change layer may be seated in a recess of a specific size provided in an area under the window and includes a prism sheet for changing a propagation path of the light emitted from the light emitting module.

According to an embodiment of the present disclosure, the light change layer includes the prism layer (or an optical member, a light change layer, or a refraction part), which is disposed in an area under the window, for changing the propagation path of the light emitted from the light emitting module.

According to an embodiment of the present disclosure, an electronic device is provided. The electronic device includes a light emitting module configured to radiate infrared light, a window disposed on the light emitting module and having a specific refractive index with respect to the infrared light, wherein the window includes a refraction part configured to totally reflect the infrared light inside the window in correspondence with the specific refractive index and a fingerprint sensor disposed under the window and configured to obtain a fingerprint (or fingerprint image, or fingerprint information) of a user based on a user input on the window by using scattered light of the infrared light totally reflected inside the window.

According to an embodiment of the present disclosure, the window includes a light transmitting layer in at least a partial area of the window, and the light emitting module is configured to radiate the infrared light through the light transmitting layer.

According to an embodiment of the present disclosure, the electronic device further includes a light guide member, and the light guide member is interposed between the window and the light emitting module.

According to an embodiment of the present disclosure, the light guide member includes at least one lens and is configured to change a direction of the infrared light radiated through the lens by the light emitting module.

According to an embodiment of the present disclosure, an electronic device is provided. The electronic device includes a window having a first specific refractive index with respect to light, a light emitting module disposed on one surface of the window and configured to radiate infrared light, a connection member having a second specific refractive index with respect to the light such that the infrared light is totally reflected inside the window in correspondence with the first specific refractive index and interposed between the window and the light emitting module and a fingerprint sensor disposed under the window and configured to obtain a fingerprint of a user based on a user input on the window by using scattered light of the infrared light totally reflected inside the window.

According to an embodiment of the present disclosure, the electronic device further includes a light transmitting layer disposed under the window corresponding to an area in which the light emitting module is disposed and passing the infrared light such that the infrared light proceeds toward the inside of the window.

According to an embodiment of the present disclosure, the light emitting module is disposed on one side surface of the window, and the electronic device further includes a light change layer configured to change a propagation direction of the infrared light.

According to an embodiment of the present disclosure, the light change layer includes a scratch pattern provided on one side of the window.

According to an embodiment of the present disclosure, the light change layer includes an optical member seated in a recess of a specific size provided in an area under the window and configured to change a propagation path of the infrared light or an optical member disposed in an area under the window and configured to change the propagation path of the infrared light.

According to an embodiment of the present disclosure, the electronic device further includes one of a reflection plate disposed on a side surface of the window and disposed such that the infrared light is totally reflected toward the inside of the window by reflecting the infrared light and a light guide member interposed between the light emitting module and a bottom surface of the window and configured to guide the infrared light toward the inside of the window.

According to an embodiment of the present disclosure, the light guide member includes a body part disposed such that one surface of the body part faces the light emitting module and including, inside the body part, a lens part configured to change a path of the infrared light and an adhesive member configured to fix the body part to the bottom surface of the window.

According to an embodiment of the present disclosure, the electronic device further includes a light guide member including the light emitting module and disposed under the window to guide the infrared light toward the inside of the window, and the light guide member includes a sensor substrate in which the light emitting module is seated, a body part surrounding the light emitting module, a lens part disposed adjacent to the body part and configured to change a propagation path of the infrared light, a lens body part configured to guide the infrared light, of which the propagation path is changed, toward the window and an adhesive member configured to fix the lens body part to a bottom surface of the window.

According to an embodiment of the present disclosure, the electronic device further includes a light guide member including the light emitting module and disposed under the window to guide the infrared light toward the inside of the window, and the light guide member includes a fixing part of which one surface is disposed to face the window, a sensor substrate which is disposed in the fixing part and in which the light emitting module is mounted, a body part surrounding the light emitting module to guide the infrared light toward the window, and an adhesive member configured to fix the body part to a bottom surface of the window.

According to an embodiment of the present disclosure, the light emitting module includes a plurality of light emitting modules disposed under one side of the window, which is adjacent to the fingerprint sensor.

According to an embodiment of the present disclosure, the electronic device further includes a proximity sensor disposed under one side of the window, and the light emitting module is disposed to emit light of a specific wavelength band toward the inside of the window through one side of a light receiving unit or a light emitting unit of the proximity sensor, or emit light to a reflection member disposed on one side of the light receiving unit or the light emitting unit of the proximity sensor and allow light reflected by the reflection member to proceed while the light is totally reflected toward the inside of the window.

According to an embodiment of the present disclosure, the electronic device further includes a speaker housing disposed on one side of the window and a reflection area disposed on one side of the speaker housing, and the light emitting module is disposed to allow light emitted to the reflection area to proceed while the light emitted to the reflection area is totally reflected toward the inside of the window after being reflected in the reflection area.

According to an embodiment of the present disclosure, the electronic device further includes a speaker housing disposed under one side of the window, and the light emitting module is disposed on one side of the speaker housing such that light emitted toward the inside of the window proceeds while being totally reflected.

According to an embodiment of the present disclosure, the electronic device further includes an illuminance sensor disposed under one side of the window, and the light emitting module disposed on one side of the illuminance sensor such that light emitted toward the inside of the window proceeds while being totally reflected.

According to an embodiment of the present disclosure, the electronic device further includes a display light emitting unit disposed in a periphery of the fingerprint sensor and configured to output a specified luminance or color with regard to an operation of the light emitting module.

Figure 9:
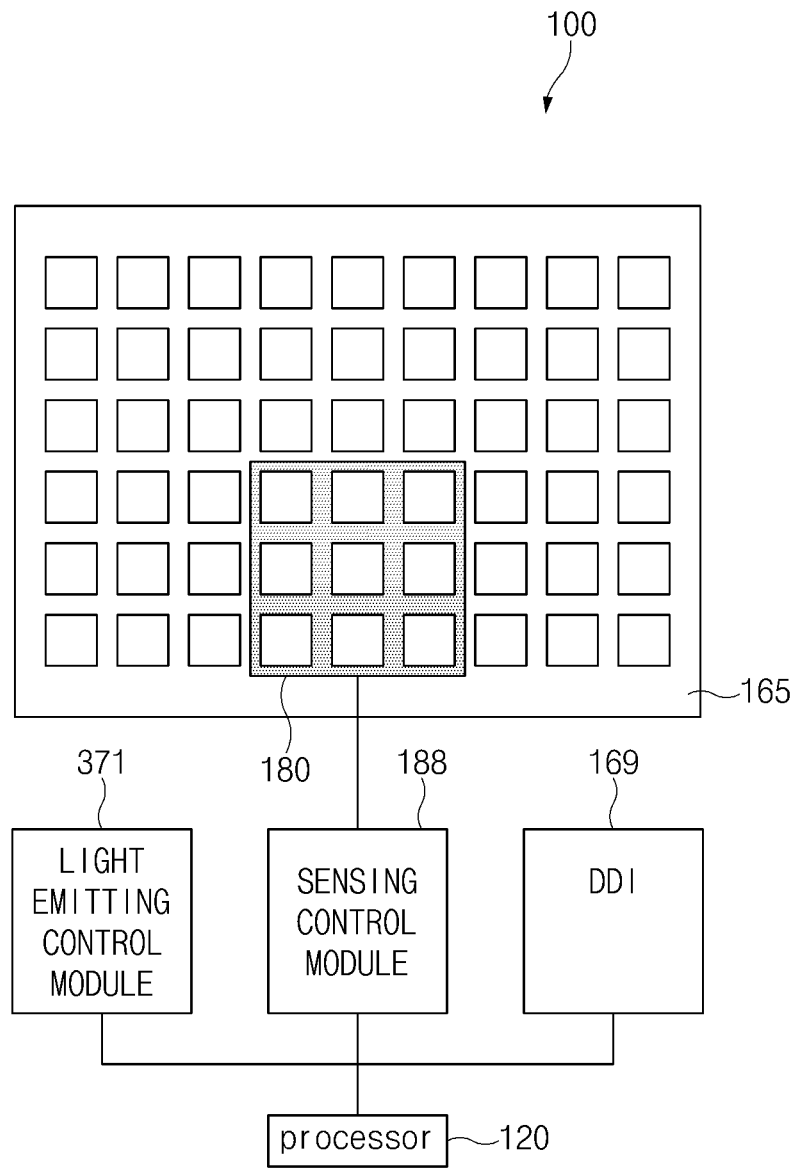
FIG. 9 illustrates a configuration associated with a processor of an electronic device, according to an embodiment of the present disclosure.

FIG. 9 illustrates a configuration associated with a processor of an electronic device, according to an embodiment of the present disclosure.

Referring to FIG. 9, the electronic device 100 includes the display panel 165, the fingerprint sensor 180, and at least one control module including light emitting control module 371, sensing control module 188, DDI 169 and processor 120.

As described above, the display panel 165 may include a panel in which at least one pixel and signal wiring lines associated with pixel driving are disposed. The fingerprint sensor 180 may be disposed in a specific area (e.g., under one side of a display area of the display panel 165) under the display panel 165.

The at least one control module may include the sensing control module 188 (or a hardware-type sensing control processor) associated with control of the fingerprint sensor 180, the display driving module 169 (or a display driving chip) associated with driving of the display panel 165, and the light emitting control module 371 (or a hardware-type light emitting control processor) associated with control of the above-described at least one light emitting module. Alternatively, the control module may include the processor 120 that controls at least one of the sensing control module 188, the display driving module 169, or the light emitting control module 371. According to an embodiment of the present disclosure, the electronic device 100 may include only at least one of each of the control modules and may be designed such that the processor 120 integrates and operates the corresponding function. The electronic device 100 may include only the display driving module 169 and the processor 120 and may be designed such that the processor 120 processes functions of the sensing control module 188 and light emitting control module 371.

The sensing control module 188 may activate the fingerprint sensor 180, may generate image information based on light that the fingerprint sensor 180 collects, and may process authentication of the generated image information. Alternatively, after generating the image information, the sensing control module 188 may transmit the generated image information to the processor 120.

The display driving module 169 may control driving of the display panel 165. According to an embodiment of the present disclosure, the display driving module 169 may output specific information based on the driving status of the fingerprint sensor 180. The display driving module 169 may output guide information (e.g., a text, an image, and the like) about the location guide of the fingerprint sensor 180. The display driving module 169 may output guide information (e.g., information for providing notification of the preparation for fingerprint sensing, information for providing notification that the fingerprint sensing is being performed, or information for providing notification whether fingerprint authentication is successful) about an operation of the fingerprint sensor 180.

The light emitting control module 371 may perform light emitting control of the light emitting module. According to an embodiment of the present disclosure, the light emitting control module 371 may control light emission of at least one light emitting module at a specific period, in real time, or in correspondence with an object approaching recognition of a proximity sensor included in the electronic device 100 or touch recognition of a touch panel, pressure sensing of a force sensor, and the like. The light emitting control module 371 may continue or stop light emission based on whether the fingerprint authentication is successful.

The processor 120 may control driving of the control modules. Alternatively, the processor 120 may process fingerprint authentication of image information that the sensing control module 188 transmits. According to an embodiment of the present disclosure, if the image information is acquired from the fingerprint sensor 180, the processor 120 may process fingerprint authentication by comparing the acquired fingerprint information with the stored fingerprint information. In this operation, the processor 120 may make a request for comparison of fingerprint information to a separate trustable operating system environment (e.g., trusted execution environment (TEE)). If the fingerprint authentication fails or if the quality of the image information acquired from the fingerprint authentication area is a specific value or less, the processor 120 may make a request for changing a display state of the fingerprint authentication area to the display driving module 169. The processor 120 may perform fingerprint authentication again based on the image information acquired by the fingerprint sensor 180 after the display state of the fingerprint authentication area is changed. The processor 120 may perform a comparison of fingerprint information for a specific number of times, and if the number of times elapses, may determine that the fingerprint authentication fails. At least one of the luminance or the color of the fingerprint authentication area may be changed for the specific number of times. If the fingerprint authentication succeeds, the processor 120 may execute a function based on the success of the fingerprint authentication.

According to an embodiment of the present disclosure, if a fingerprint authentication request occurs, the processor 120 may adjust the sensitivity of the touch sensor (e.g., adjust the sensitivity such that the change according to the object approaching (non-contact) a touch sensor is sensed, by setting the sensor IC or the processor to finely sense a change in capacitance). The processor 120 may identify whether a hovering event according to the object approaching occurs by adjusting the touch sensitivity of the fingerprint authentication area. Alternatively, the processor 120 may identify whether a touch event occurs in the fingerprint authentication area. Alternatively, if the fingerprint authentication request occurs, the processor 120 may activate the fingerprint sensor 180 and the light emitting module 300 and may determine whether an object such as a finger approaches, based on image information that the fingerprint sensor 180 obtains. If at least one of a hovering event, a touch event, or a finger approach event occurs, the processor unit 120 may transmit the corresponding event to the display driving module 169. If the state of the fingerprint authentication area is changed by the display driving module 169, the processor 120 may restore the state of the touch sensor area, of which the sensitivity has been adjusted, to an original state. Further, if the fingerprint authentication is completed, the processor 120 may restore the state of the touch sensor area, of which the sensitivity has been adjusted, to an original state.

Figure 10:
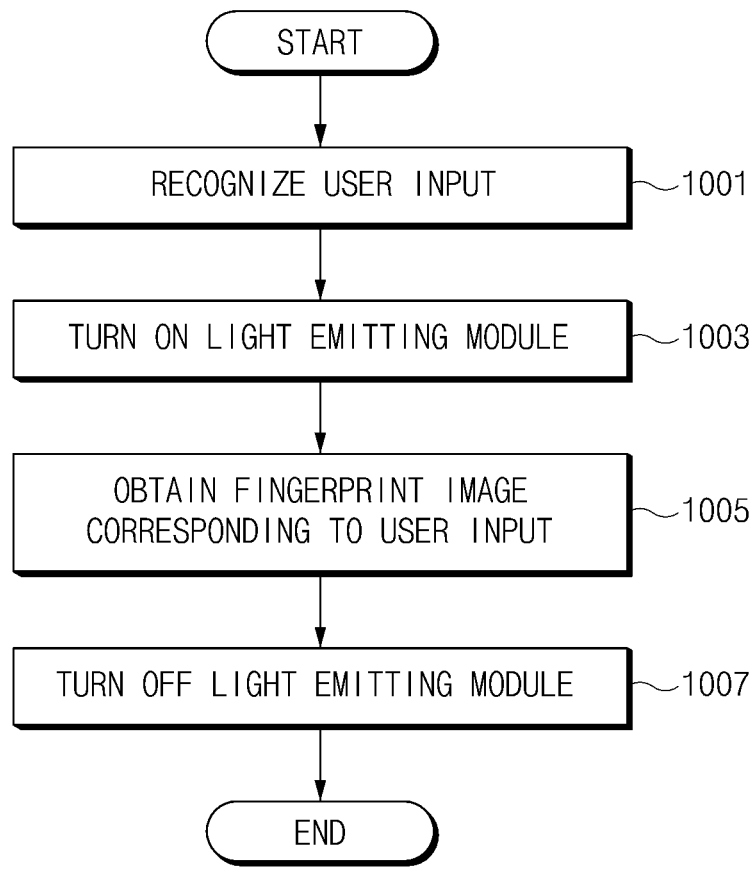
FIG. 10 is a flowchart illustrating an electronic device operating method associated with fingerprint sensing, according to an embodiment of the present disclosure.

FIG. 10 is a flowchart illustrating an electronic device operating method associated with fingerprint sensing, according to an embodiment of the present disclosure.

Referring to FIG. 10, in the electronic device operating method, in step 1001, the processor 120 of the electronic device 100 recognizes a user input. The processor 120 may recognize an object approaching a proximity sensor included in the electronic device 100 or touch recognition of a touch panel, pressure sensing of a force sensor, and the like as a user input at a specific period or in real time.

In step 1003, the processor 120 turns on a light emitting module in response to the user input. The light emitted from the turned-on light emitting module may proceed while being totally reflected inside the window 161. As such, in the case where an object such as a finger touches a specific area of the window 161, the light emitted from the light emitting module 300 disposed in a periphery of the electronic device 100 may reach the surface of the object while being totally reflected, and the light reflected or scattered from the surface of the object may be incident in a direction of the fingerprint sensor 180. The processor 120 may activate the fingerprint sensor 180 when turning on the light emitting module 300.

In step 1005, the processor 120 obtains a fingerprint image corresponding to the user input. The sensing control module 188 connected with the fingerprint sensor 180 may generate a fingerprint image based on the obtained light and may transmit the generated image to the processor 120. Alternatively, the processor 120 may obtain the fingerprint image that the fingerprint sensor 180 obtains, by directly controlling the fingerprint sensor 180. The processor 120 may determine whether fingerprint authentication is successful, by verifying the obtained fingerprint image and fingerprint information that is stored in advance. The processor 120 may perform processing based on whether the fingerprint authentication is successful. For example, when the fingerprint authentication is successful, the processor 120 may activate a specific user function. Alternatively, when the fingerprint authentication fails, the processor 120 may perform processing associated with acquisition of the fingerprint image again or may control output of information about fingerprint authentication failure.

In step 1007, the processor 120 turns off the light emitting module. When the fingerprint authentication is successful, the processor 120 may deactivate the light emitting module by turning off electric power to the light emitting module. Additionally, the processor 120 may deactivate the fingerprint sensor 180.

According to an embodiment of the present disclosure, a method of operating an electronic device includes receiving a user input, activating a light emitting module disposed in an area under a periphery of a window to allow light emitted from the light emitting module to be totally reflected inside the window, generating a fingerprint image by collecting light reflected on a surface of a finger disposed on the window while the light is totally reflected inside the window, and performing fingerprint authentication associated with the fingerprint image.

Figure 11:
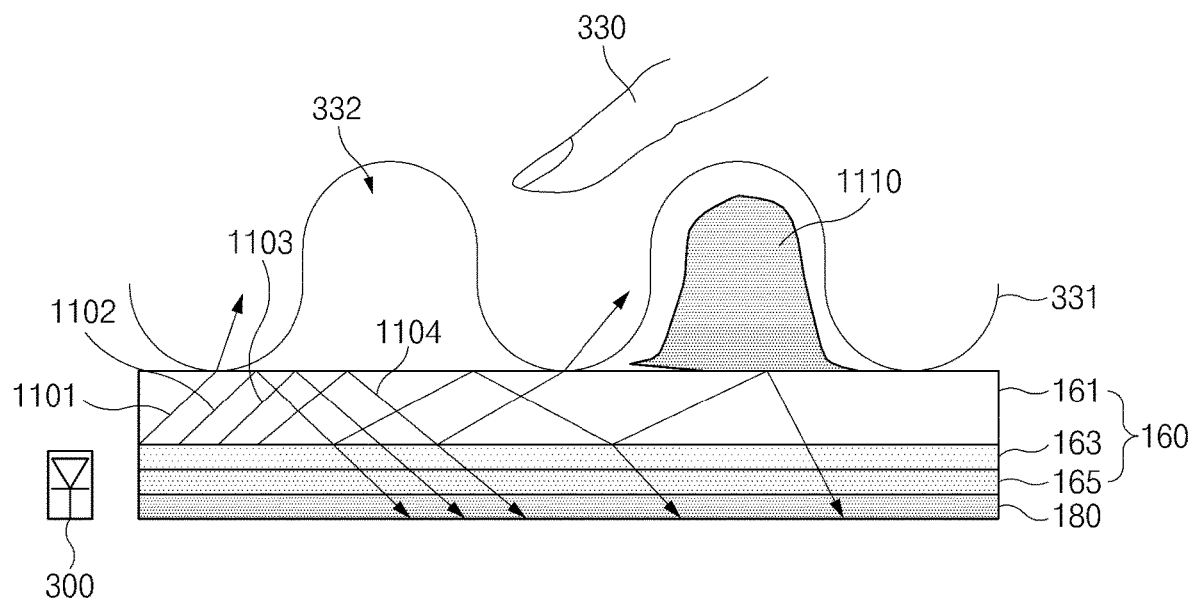
FIG. 11 illustrates light propagation associated with fingerprint sensing, according to an embodiment of the present disclosure.

FIG. 11 illustrates light propagation associated with fingerprint sensing, according to an embodiment of the present disclosure.

Referring to FIG. 11, if a request associated with fingerprint authentication occurs, the processor 120 of the electronic device 100 may control the light emission of the light emitting module 300. The light emitting module 300 may emit light to be entered in a direction of the window 161 from an area under the window 161 with a specific inclination, and the emitted light may proceed while being totally reflected inside the window 161. In the above-described process, in the case where a foreign object is on a surface of finger 330, since a path of the light proceeding from the foreign object is changed while total internal reflection of the light transmitted through the window 161 is changed, the light may proceed in the direction of the fingerprint sensor 180. As such, even though the foreign object is disposed on a fingerprint surface, the fingerprint sensor 180 may obtain image information about the fingerprint surface.

According to an embodiment of the present disclosure, first light 1101 of the light that is totally reflected through the window 161 after being emitted from the light emitting module 300 may be absorbed into a surface of the ridge 331 in a fingerprint of a finger 330 touching the surface of the window 161. While second light 1102 of the light that is totally reflected through the window 161 after being emitted from the light emitting module 300 is totally reflected on a boundary surface between the window 161 and a valley 332, at least part of the second light 1102 may proceed to the fingerprint sensor 180 on a surface between the window 161 and the bonding layer 163, and the remaining at least part of the second light 1102 may be totally reflected. After a propagation direction of the second light 1102 is changed at a boundary surface between a foreign object 1110 and the window 161, the second light 1102 may proceed to the fingerprint sensor 180. As such, since the second light 1102 is not absorbed on the boundary surface between the window 161 and the foreign object 1110, the shape corresponding to a normal valley 332 may be distinguished by the fingerprint sensor 180. After proceeding while being totally reflected on the boundary surface between the window 161 and the valley 332, third light 1103 of the totally reflected light may proceed from the boundary surface between the window 161 and the bonding layer 163 to the fingerprint sensor 180. In this case, while being totally reflected on the boundary surface between the window 161 and the bonding layer 163, at least a portion of the third light 1103 may proceed to the inside of the window 161. After being totally reflected on the boundary surface between the window 161 and the valley 332 and on the boundary surfaces between the window 161 and the bonding layer 163, at least a portion of fourth light 1104 may be absorbed into the ridge 331 of the surface of the finger 330. The light, which is absorbed by the ridge 331, may be recognized as a shaded area by the fingerprint sensor 180. The light that proceeds to the fingerprint sensor 180 on the boundary surface between the window 161 and the bonding layer 163 after a propagation path is changed at a surface of the window 161 that the valley 332 or the foreign object 1110 meets may be recognized as a non-shaded area by the fingerprint sensor 180. As such, the fingerprint sensor 180 may generate image information obtained by distinguishing the valley 332 from the ridge 331 regardless of whether the foreign object 1110 is present.

Figure 12:
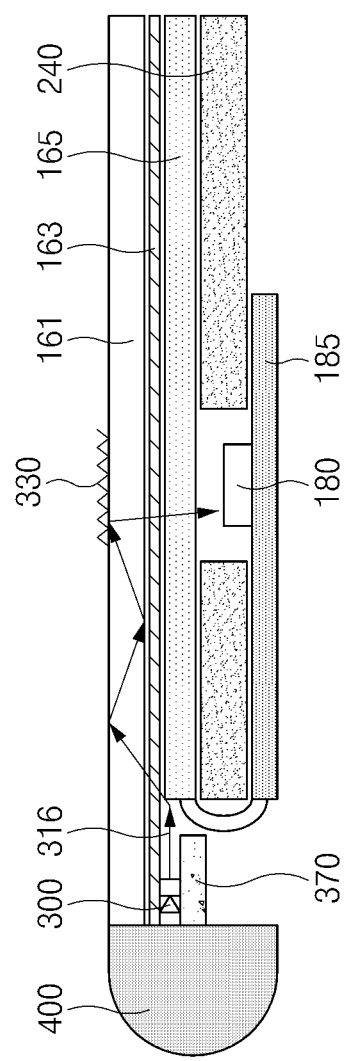
FIG. 12 illustrates a structure of an electronic device in which a light emitting module is disposed on a side surface, according to an embodiment of the present disclosure.

FIG. 12 illustrates a structure of an electronic device in which a light emitting module is disposed on a side surface, according to an embodiment of the present disclosure.

Referring to FIG. 12, the electronic device includes the window 161, the bonding layer 163, the display panel 165, the bracket 240, the substrate 185 (or the display substrate), the fingerprint sensor 180, a housing 400, the sensor substrate 370, the light emitting module 300, and a first light guide member 316. The window 161, the bonding layer 163, the display panel 165, the bracket 240, the fingerprint sensor 180, and the like may include a configuration substantially the same as or similar to the components described in FIGS. 2A to 3B above. The substrate 185 may be provided in a flexible form, and may transmit a signal associated with driving of the fingerprint sensor 180. The substrate 185 may be connected with the display panel 165 and may include a display substrate that transmits the signal associated with the driving of the fingerprint sensor 180. The fingerprint sensor 180 may be mounted on one side of the substrate 185. The bracket 240 may include a recess or a hole in which the fingerprint sensor 180 is disposed.

The housing 400 may be disposed to face a periphery of the window 161, the display panel 165, and may include a space in which components of the electronic device are seated. The light emitting module 300 may be disposed on a side wall of the housing 400.

The sensor substrate 370 may supply electric power associated with control of the light emitting module 300. The sensor substrate 370 may be electrically connected with the substrate 185 or the above-described main printed circuit board 210 and may transmit a signal and electric power necessary for driving of the light emitting module 300.

The light emitting module 300 may be interposed between the display panel 165 and the sensor substrate 370. The light emitting module 300 may be disposed to emit light in a horizontal direction (e.g., a right direction with respect to FIG. 12). According to an embodiment of the present disclosure, the light emitting module 300 may be disposed to face a side surface of the display panel 165. The light emitted from the light emitting module 300 may be incident on the window 161 through the first light guide member 316, and the propagation path of the light may be changed when the light incident on the window 161 is reflected from an object such as the finger 330 while being totally reflected inside the window 161.

The first light guide member 316 may be formed such that the surface of the first light guide member 316 facing the light emitting module 300 is vertical. The first light guide member 316 may be formed such that the surface of the first light guide member 316 facing the light emitting module 300 has a specific inclination with respect to the vertical direction. As such, the light of the light emitting module 300 emitted through one side of the first light guide member 316 may be incident in a direction of the window 161, after the propagation direction of the light is changed at a surface having an inclination of the first light guide member 316. In the case, at least part of the display panel 165 may be formed to be transparent, and thus the light emitted from the light emitting module 300 may be incident on the window 161 after passing through the display panel 165. An adhesive may be applied to at least one of a surface facing the display panel 165 and a surface facing the sensor substrate 370 among the first light guide member 316.

Figure 13:
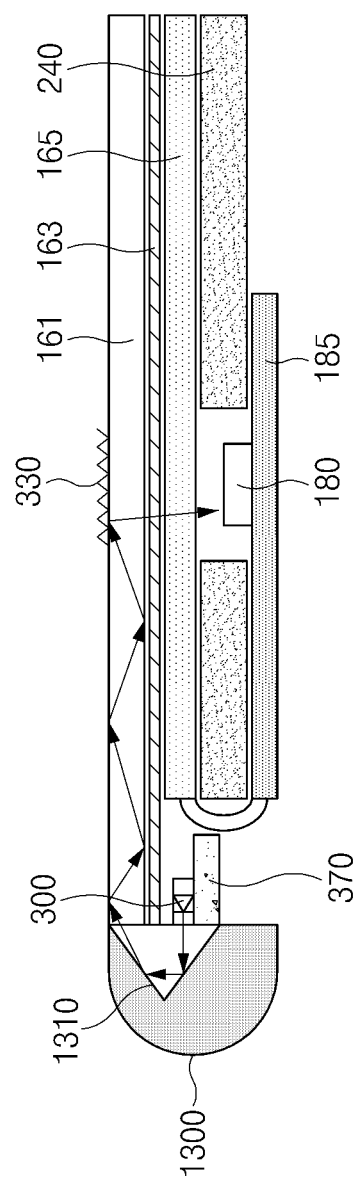
FIG. 13 illustrates a structure of an electronic device in which a light guide member is disposed inside a housing, according to an embodiment of the present disclosure.

FIG. 13 illustrates a structure of an electronic device in which a light guide member is disposed inside a housing, according to an embodiment of the present disclosure.

Referring to FIG. 13, the electronic device includes the window 161, the bonding layer 163, the display panel 165, the bracket 240, the substrate 185 (or the display substrate), the fingerprint sensor 180, a housing 1300, the sensor substrate 370, the light emitting module 300, and a second light guide member 1310. The window 161, the bonding layer 163, the display panel 165, the bracket 240, the fingerprint sensor 180, the substrate 185, the sensor substrate 370, and the like may include a configuration substantially the same as or similar to components described in FIGS. 2A to 3B and FIG. 12.

The housing 1300 may be disposed to face a periphery of the window 161, the display panel 165, and may include a space in which components of the electronic device are seated. The light emitting module 300 may be disposed in an area adjacent to the housing 1300. The housing 1300 may include a recess of a specific size in which the second light guide member 1310 is disposed.

The second light guide member 1310 may include an optical member (e.g., a prism pattern) and may be disposed inside the housing 1300. The second light guide member 1310 may be provided such that the light emitted from the light emitting module 300 is incident toward the inside of the window 161 after being refracted. Additionally, a bonding layer may be disposed on a surface facing the light emitting module 300 such that the second light guide member 1310 fixes the light emitting module 300.

The light emitting module 300 may be interposed between the display panel 165 and the sensor substrate 370. The light emitting module 300 may be disposed to emit light in a horizontal direction (e.g., a left direction with respect to FIG. 13). According to an embodiment of the present disclosure, the light emitting module 300 may emit light in a direction of the second light guide member 1310 disposed in the housing 1300. The light emitted from the light emitting module 300 may proceed to the inside of the second light guide member 1310, and the light may be incident toward the inside of the window 161 after being refracted in a periphery of the second light guide member 1310. In this process, the light may be incident toward the inside of the window 161 after being refracted at least a plurality of times. After the light incident toward the inside of the window 161 is reflected, refracted, and absorbed (e.g., refracted or absorbed according to a valley or a ridge) on a surface of the finger 330 while being totally reflected, at least a portion of the light may proceed to the fingerprint sensor 180.

Figure 14:
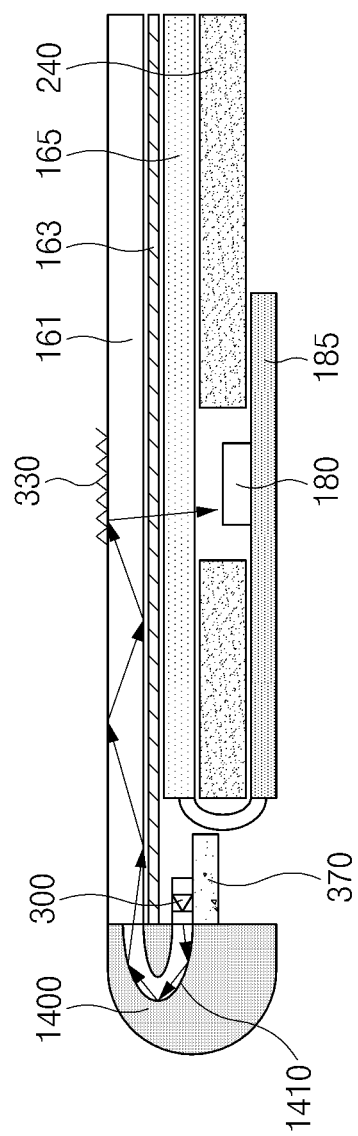
FIG. 14 illustrates a structure of an electronic device in which a light guide member is disposed inside a housing, according to an embodiment of the present disclosure.

FIG. 14 illustrates a structure of an electronic device in which a light guide member is disposed inside a housing, according to another embodiment of the present disclosure.

Referring to FIG. 14, the electronic device includes the window 161, the bonding layer 163, the display panel 165, the bracket 240, the substrate 185 (or the display substrate), the fingerprint sensor 180, a housing 1400, the sensor substrate 370, the light emitting module 300, and a third light guide member 1410. The window 161, the bonding layer 163, the display panel 165, the bracket 240, the fingerprint sensor 180, the substrate 185, the sensor substrate 370, and the like may include a configuration substantially the same as or similar to components described in FIGS. 2A to 3B and FIGS. 12 and 13.

The housing 1400 may be disposed to face a periphery of the window 161, the display panel 165, and may include a space in which components of the electronic device are seated. The light emitting module 300 may be disposed in an area adjacent to the housing 1400. The housing 1400 may include a hole of a specific size in which the third light guide member 1400 is disposed.

The third light guide member 1410 may allow the light emitted from the light emitting module 300 to be incident toward the inside of the window 161, by serving as a waveguide. At least part of the third light guide member 1410 may be formed of optical fiber or transparent plastic material. One side of the waveguide-shaped third light guide member 1410 may face an area of light emission of the light emitting module 300 or may be attached to the area of the light emitting module 300. The other side of the third light guide member 1410 may face a side surface of the window 161 or may be fixed to the side surface of the window 161.

The light emitting module 300 may be interposed between the display panel 165 and the sensor substrate 370. The light emitting module 300 may be disposed to emit light in a horizontal direction (e.g., a left direction with respect to FIG. 14). The light that the light emitting module 300 emits may proceed to the inside of the third light guide member 1410 and may be incident toward the inside of the window 161 while proceeding along the inside of the path-shaped third light guide member 1410. In this process, the light may be incident toward the inside of the window 161 after being refracted at least a plurality of times. The light incident toward the inside of the window 161 may be reflected, refracted, and absorbed (e.g., refracted or absorbed according to a valley or a ridge) on the finger 330 surface while being totally reflected, and at least a portion of the light may proceed to the fingerprint sensor 180.

Figure 15:
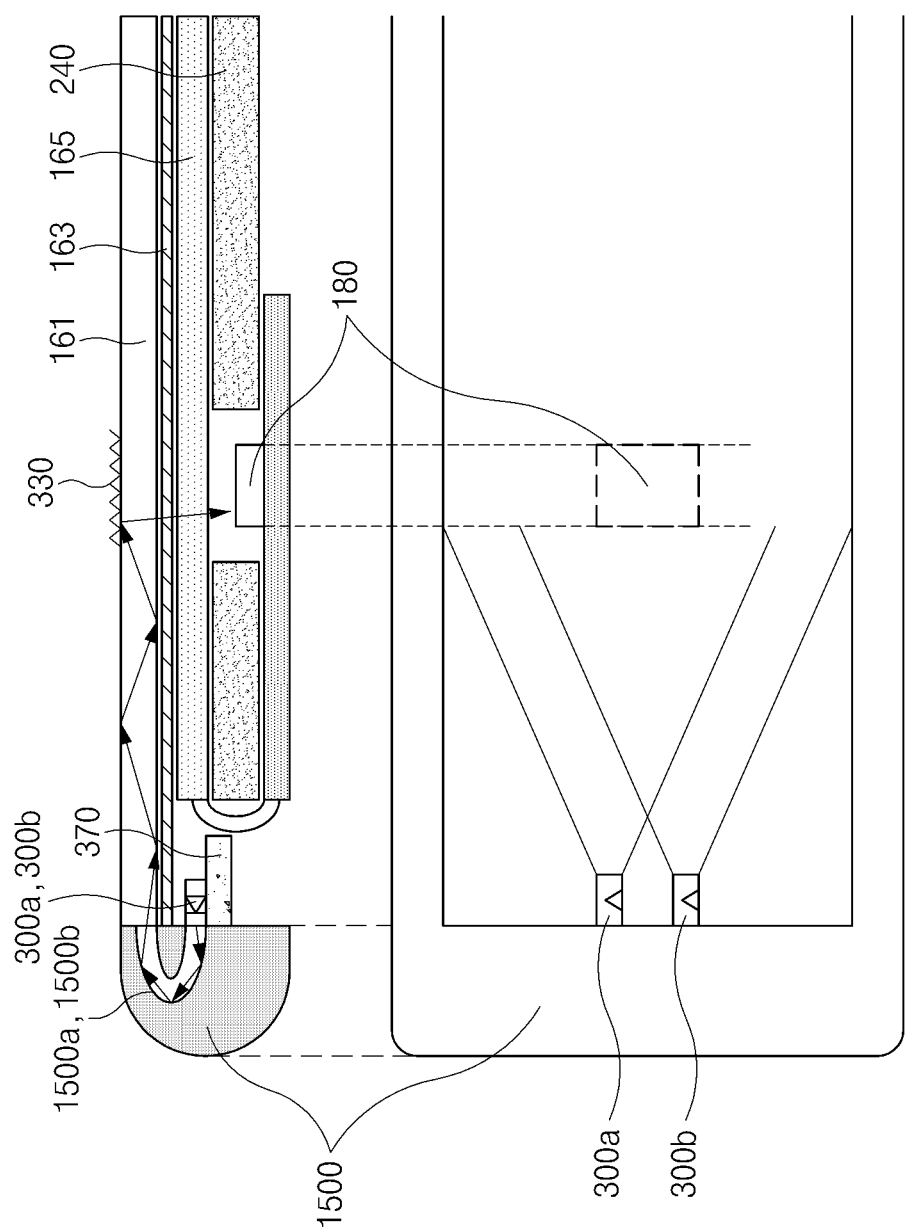
FIG. 15 illustrates a structure of an electronic device in which a light guide member is disposed inside a housing, according to an embodiment of the present disclosure.

FIG. 15 illustrates a structure of an electronic device in which a light guide member is disposed inside a housing, according to another embodiment of the present disclosure.

Referring to FIG. 15, the electronic device includes the window 161, the bonding layer 163, the display panel 165, the bracket 240, the substrate 185 (or the display substrate), the fingerprint sensor 180, a housing 1500, the sensor substrate 370, light emitting modules 300a and 300b, and a plurality of fourth light guide members 1500a and 1500b. The window 161, the bonding layer 163, the display panel 165, the bracket 240, the fingerprint sensor 180, the substrate 185, the sensor substrate 370, and the like may include a configuration substantially the same as or similar to components described in FIGS. 2A to 3B and FIG. 14.

The housing 1500 may be disposed to face a periphery of the window 161, the display panel 165, and may include a space in which components of the electronic device are seated. The light emitting modules 300a and 300b may be disposed in an area adjacent to the housing 1500. The housing 1500 may include a plurality of holes in which the plurality of fourth light guide members 1500a and 1500b are disposed. The holes may be provided as an inlet at one side wall of the housing 1500 (e.g., a side wall facing the light emitting modules 300a and 300b) and may be provided as an outlet at an area (e.g., the side wall of the housing 1500 facing the window 161 with respect to FIG. 15) adjacent to an area to which the inlet is provided.

The fourth light guide members 1500a and 1500b may be substantially the same as or similar to the third light guide member 1410 described in FIG. 14. However, each of the fourth light guide members 1500a and 1500b may include a plurality of light guide members, each of the fourth light guide members 1500a and 1500b may serve as a path for moving light emitted from the plurality of light emitting modules 300a and 300b.

Each of the light emitting modules 300a and 300b may include a plurality of light emitting modules, and the plurality of light emitting modules may be interposed between the display panel 165 and the sensor substrate 370. The light emitting modules 300a and 300b may be disposed to emit light to the fourth light guide members 1500a and 1500b, in which holes are disposed, in a horizontal direction. The light that the light emitting modules 300a and 300b emit may be incident toward the inside of the window 161 at different locations through the fourth light guide members 1500a and 1500b. After the light incident toward the inside of the window 161 is reflected, refracted, and absorbed (e.g., refracted or absorbed according to a valley or a ridge) on the finger 330 surface while being totally reflected, at least a portion of the light may proceed to the fingerprint sensor 180.

Figure 16:
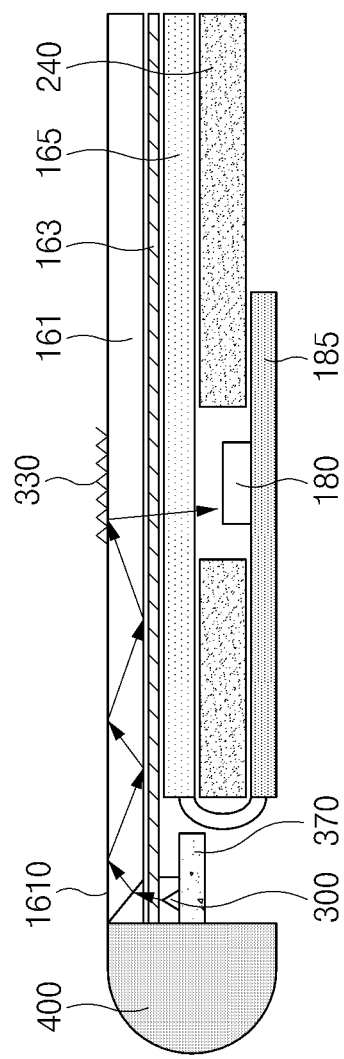
FIG. 16 illustrates a structure of an electronic device including a window in which light propagation is changed, according to an embodiment of the present disclosure.

FIG. 16 illustrates a structure of an electronic device including a window in which light propagation is changed, according to an embodiment of the present disclosure.

Referring to FIG. 16, the electronic device includes a window 1600, the bonding layer 163, the display panel 165, the bracket 240, the substrate 185 (or the display substrate), the fingerprint sensor 180, the housing 400, the sensor substrate 370, and the light emitting module 300. The housing 400, the bonding layer 163, the display panel 165, the bracket 240, the fingerprint sensor 180, the substrate 185, the sensor substrate 370, and the like may include a configuration substantially the same as or similar to components described in FIGS. 2A to 3B and FIG. 12.

The light emitting module 300 may be interposed between the display panel 165 and the sensor substrate 370. The light emitting module 300 may be disposed to emit light in a vertical direction (e.g., an upper-side direction in which the window 1600 is disposed, with respect to FIG. 16). According to an embodiment of the present disclosure, a light guide member associated with light transmission may be interposed between the light emitting module 300 and the display panel 165.

The window 1600 may be formed such that top and bottom surfaces of the window 1600 are flat. The window 1600 may be disposed to be parallel with the display panel 165. A first optical member 1610 (or a refraction part or a light change layer) may be disposed in at least part of a periphery of the window 1600. The first optical member 1610 may include a pattern disposed inside the window 1600. The first optical member 1610 may be provided to cross the upper side and the lower side of the window 1600 and to have a specific inclination. The first optical member 1610 may be provided to change a propagation path of the light emitted from the light emitting module 300.

After the propagation direction of the light is changed at one surface of the first optical member 1610, the light emitted from the light emitting module 300 may be totally reflected toward the inside of the window 1600. The totally reflected light is reflected, refracted, and absorbed on the surface of the finger 330, and at least part of the reflected or refracted light may proceed to the fingerprint sensor 180.

Figure 17:
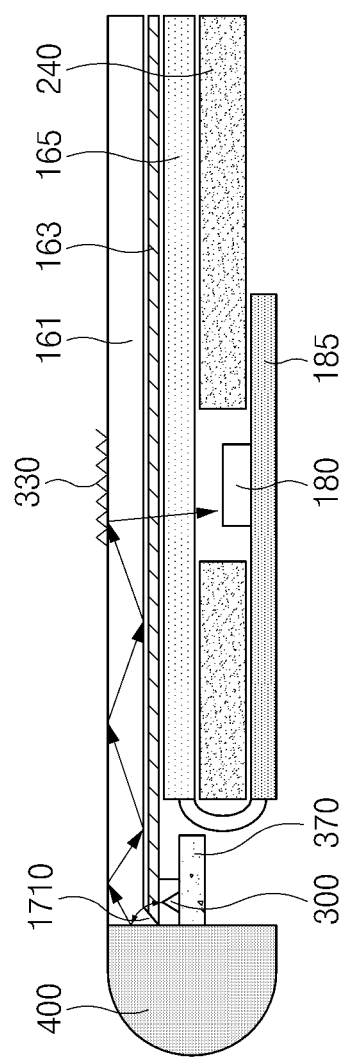
FIG. 17 illustrates a structure of an electronic device including a window in which light propagation is changed, according to an embodiment of the present disclosure.

FIG. 17 illustrates a structure of an electronic device including a window in which light propagation is changed, according to another embodiment of the present disclosure.

Referring to FIG. 17, the electronic device includes a window 1700, the bonding layer 163, the display panel 165, the bracket 240, the substrate 185 (or the display substrate), the fingerprint sensor 180, the housing 400, the sensor substrate 370, and the light emitting module 300. The housing 400, the bonding layer 163, the display panel 165, the bracket 240, the fingerprint sensor 180, the substrate 185, the sensor substrate 370, and the like may include a configuration substantially the same as or similar to components described in FIGS. 2A to 3B and FIG. 12.

The light emitting module 300 may be interposed between the display panel 165 and the sensor substrate 370. The light emitting module 300 may be disposed to emit light in a vertical direction (e.g., an upper-side direction in which the window 1700 is disposed, with respect to FIG. 17). According to an embodiment of the present disclosure, a light guide member associated with light transmission may be interposed between the light emitting module 300 and the display panel 165. At least a portion of the light emitting module 300 may be disposed to directly contact one side of a periphery of the window 1700. Alternatively, at least a portion of the light emitted from the light emitting module 300 may be directly incident on the periphery of the window 1700. A light guide member may be interposed between the light emitting module 300 and the periphery of the window 1700.

The window 1700 may be formed such that top and bottom surfaces of the window 1700 are flat. The window 1700 may be disposed to be parallel with the display panel 165. A second optical member 1710 may be disposed in at least part of a periphery of the window 1700. The second optical member 1710 may include at least one protrusion protruding downward (e.g., a direction in which the light emitting module 300 is disposed) with respect to the bottom surface of the periphery of the window 1700. According to an embodiment of the present disclosure, at least one surface of the second optical member 1710 may be disposed to directly face an area in which the light is emitted from the light emitting module 300. In this regard, the bonding layer 163 and the display panel 165 may be disposed in a form in which at least part of the bonding layer 163 and the display panel 165 are removed.

The light emitted from the light emitting module 300 may be totally reflected toward the inside of the window 1700 after the propagation direction of the light is first changed at one surface of the second optical member 1710 and then the propagation direction of the light is changed again at a second surface of the second optical member 1710. The totally reflected light is reflected, refracted, and absorbed on the surface of the finger 330, and at least part of the reflected or refracted light may proceed to the fingerprint sensor 180.

Figure 18:
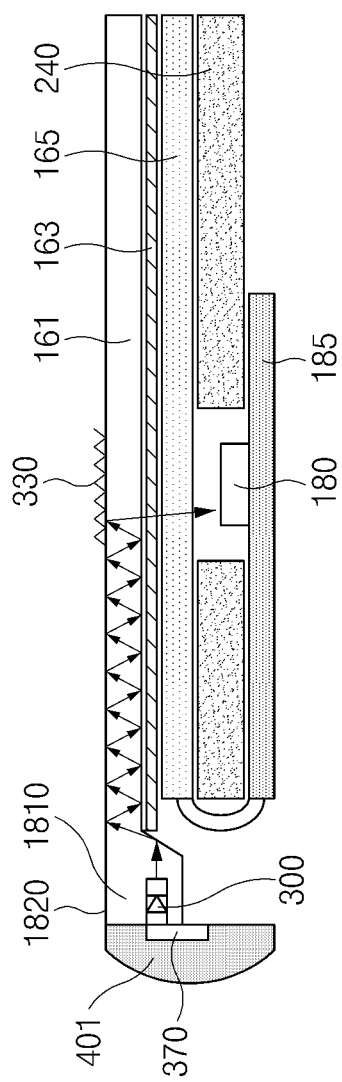
FIG. 18 illustrates a structure of an electronic device including a window in which light propagation is changed, according to an embodiment of the present disclosure.

FIG. 18 illustrates a structure of an electronic device including a window in which light propagation is changed, according to another embodiment of the present disclosure.

Referring to FIG. 18, the electronic device includes a window 1800, the bonding layer 163, the display panel 165, the bracket 240, the substrate 185 (or the display substrate), the fingerprint sensor 180, a housing 401, the sensor substrate 370, and the light emitting module 300. The bonding layer 163, the display panel 165, the bracket 240, the fingerprint sensor 180, the substrate 185, the sensor substrate 370, may include a configuration substantially the same as or similar to components described in FIGS. 2A to 3B. For example, each of the bonding layer 163 and the display panel 165 may have an area smaller than an area of the window 1800.

The window 1800 may have a specific thickness and surface and may be disposed over the display panel 165 while the bonding layer 163 is interposed between the window 1800 and the display panel 165. The housing 401 may be disposed in a periphery of the window 1800. According to an embodiment of the present disclosure, the window 1800 may be formed such that the thickness of a periphery of the window 1800 is different from the thickness of a center of the window 1800. The window 1800 may be formed such that the thickness of the periphery is thicker than the thickness of the center (or an area adjacent to the center). The light emitting module 300 may be disposed inside a peripheral area of the window 1800. With regard to the arrangement of the light emitting module 300, a recess in which the light emitting module 300 is capable of being inserted may be formed on one side of the window 1800. A step having a specific inclination may be formed on one side of the window 1800 into which the light emitting module 300 is inserted. As such, the light emitted in a direction of the center of the window 1800 from the light emitting module 300 may proceed while being totally reflected toward the inside of the window 1800 after being refracted on the surface of the step formed in one side of the window 1800. While the light totally reflected toward the inside of the window 1800 is reflected, refracted, and absorbed on the surface of the finger 330, at least a portion of the light may proceed to the fingerprint sensor 180.

As described above, the at least one light emitting module 300 may be disposed on one side of a periphery of the window 1800. In this case, the light emitting module 300 may be inserted into the periphery of the window 1800 and may emit light in a direction of the center of the window 1800. A rear surface (e.g., a surface facing the direction opposite to a direction in which light is emitted) of the light emitting module 300 may be disposed to face a side wall of the housing 401. Alternatively, a bonding layer may be interposed between the rear surface of the light emitting module 300 and the side wall of the housing 401 to fix the light emitting module 300.

At least part of the housing 401 may be disposed to surround the side surface of the window 1800. One side of the housing 401 may be disposed adjacent to the light emitting module 300 inserted in the window 1800. According to an embodiment of the present disclosure, the sensor substrate 370 associated with the driving of the light emitting module 300 may be disposed on one side of the housing 401. In this regard, a recess in which the sensor substrate 370 is disposed may be disposed on one side of the housing 401.

The sensor substrate 370 may be disposed on one side of the housing 401, and the light emitting module 300 may be mounted in the sensor substrate 370. An IC associated with the driving of the light emitting module 300 may be mounted in the sensor substrate 370. According to an embodiment of the present disclosure, the sensor substrate 370 may be electrically connected with the substrate 185 or may be electrically connected with a main printed circuit board 210. The sensor substrate 370 may transmit a driving signal received from a driving module (e.g., an IC) disposed on the substrate 185 or the main printed circuit board 210 to the light emitting module 300.

A print area 1820 may be disposed on one side of the window 1800, for example, a top surface of a periphery of the window 1800. The print area 1820 may prevent the light emitting module 300 from being observed from the outside. In this regard, a recess that the print area 1820 is capable of being disposed may be provided in the window 1800, and the print area 1820 may be printed in the recess. According to an embodiment of the present disclosure, the print area 1820 may include a black matrix or a specific print pattern.

Figure 19:
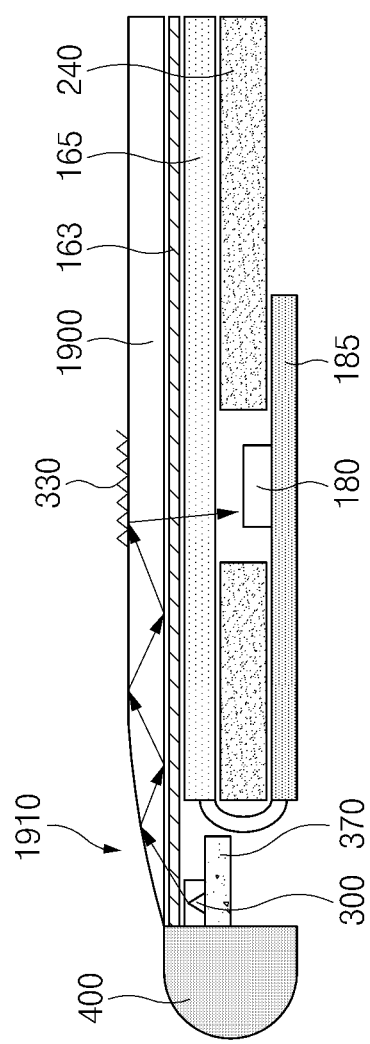
FIG. 19 illustrates a structure of an electronic device in which a light emitting module is disposed on a side surface, according to an embodiment of the present disclosure.

FIG. 19 illustrates a structure of an electronic device in which a light emitting module is disposed on a side surface, according to an embodiment of the present disclosure.

Referring to FIG. 19, the electronic device includes a window 1900, the bonding layer 163, the display panel 165, the bracket 240, the substrate 185 (or the display substrate), the fingerprint sensor 180, the housing 400, the sensor substrate 370, and the light emitting module 300. The bonding layer 163, the display panel 165, the bracket 240, the fingerprint sensor 180, the substrate 185, the sensor substrate 370, and the like may include a configuration substantially the same as or similar to components described in FIGS. 2A to 3B and FIG. 12.

The light emitting module 300 may be interposed between the display panel 165 and the sensor substrate 370. The light emitting module 300 may be disposed to emit light in a vertical direction (e.g., an upper-side direction of the window 1900 with respect to FIG. 19). According to an embodiment of the present disclosure, the light emitting module 300 may be disposed to face a bottom surface of a periphery of the display panel 165. The light emitted from the light emitting module 300 may be incident on the window 1900 after passing through at least part of the transparent area of the bonding layer 163. The light incident on the window 1900 may be reflected, refracted, and absorbed while being totally reflected inside the window 1900 after a propagation angle is changed on the curved surface of the window 1900 resulting in at least part of the light proceeding to the fingerprint sensor 180.

A flat area may be disposed in the center of the window 1900, and a peripheral area of the window 1910 may be provided in a curved form. Alternatively, at least part of the window 1900 may be provided in the curved form. Alternatively, as it goes to a periphery of the window 1900 from the center of the window 1900, the window 1900 may be provided in a curved form. In FIG. 19, it is illustrated that the peripheral area 1910 of the window 1900 is curved. The propagation path of the light emitted from the bottom surface of the window 1900 may be changed at the curved peripheral area 1910 of the window 1900. The light of which the propagation path is changed may proceed while being totally reflected inside the window 1900.

Figure 20A:
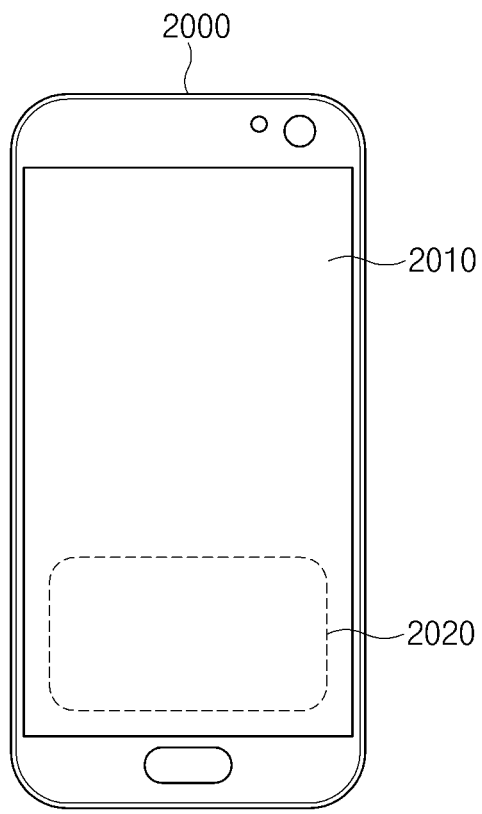
FIG. 20A illustrates an electronic device associated with a fingerprint sensor, according to an embodiment of the present disclosure.

FIG. 20A illustrates an electronic device associated with a fingerprint sensor, according to an embodiment of the present disclosure.

Referring to FIG. 20A, a biometric sensor 2020 (e.g., a fingerprint sensor) for recognizing biometric information (e.g., fingerprint information) may be formed in at least a partial area of a display 2010 of the electronic device 2000. The biometric sensor 2020 may be formed in at least part (e.g., an active area or a black matrix (BM) area of a display) of the display 2010, and thus the biometric sensor 2020 may obtain biometric information of a user by using a user input to the display 2010. As shown in FIG. 20A, the biometric sensor 2020 may be provided on the display 2010 such that the size of the biometric sensor 2020 is not less than a specific size. As such, the biometric sensor 2020 may simultaneously obtain fingerprint image information about a plurality of fingers (e.g., the first finger, the second finger, the third finger, and the like).

Figure 20B:
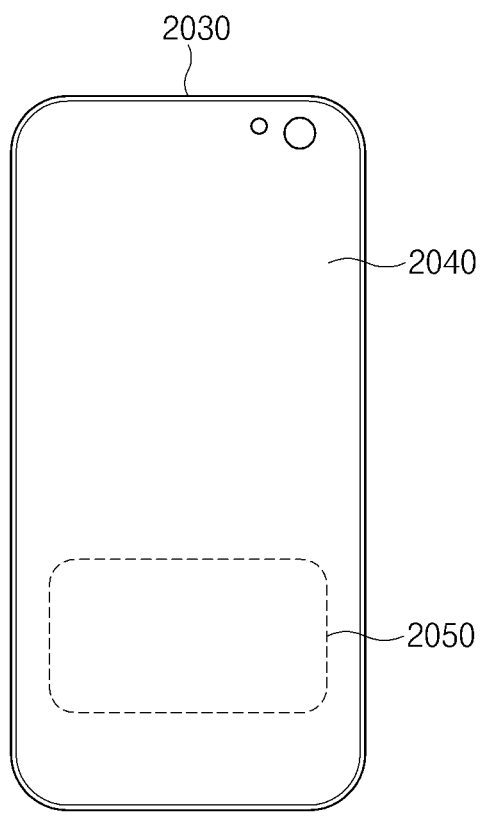
FIG. 20B illustrates an electronic device associated with a fingerprint sensor, according to an embodiment of the present disclosure.

FIG. 20B illustrates an electronic device associated with a fingerprint sensor, according to another embodiment of the present disclosure.

Referring to FIG. 20B, an electronic device 2030 includes a biometric sensor 2050 in at least part of the display 2040. As illustrated in FIG. 20B, the electronic device 2030 may place an area that the biometric sensor 2050 occupies, in a specific area of the display 2040. It is exemplified as the electronic device 2030 extends to a lower portion area of the display 2040. The biometric sensor 2050 may be disposed toward the lower portion of the display 2040 in consideration of the area of the display 2040. Alternatively, the biometric sensor 2050 may be disposed at a specific location that a thumb and the like reaches when a user grips the electronic device 2030. Since the biometric sensor 2050 of a specific size or more is disposed therein, the electronic device 2030 may perform fingerprint sensing freely regardless of the size of a finger, a hand, and the like.

Figure 21:
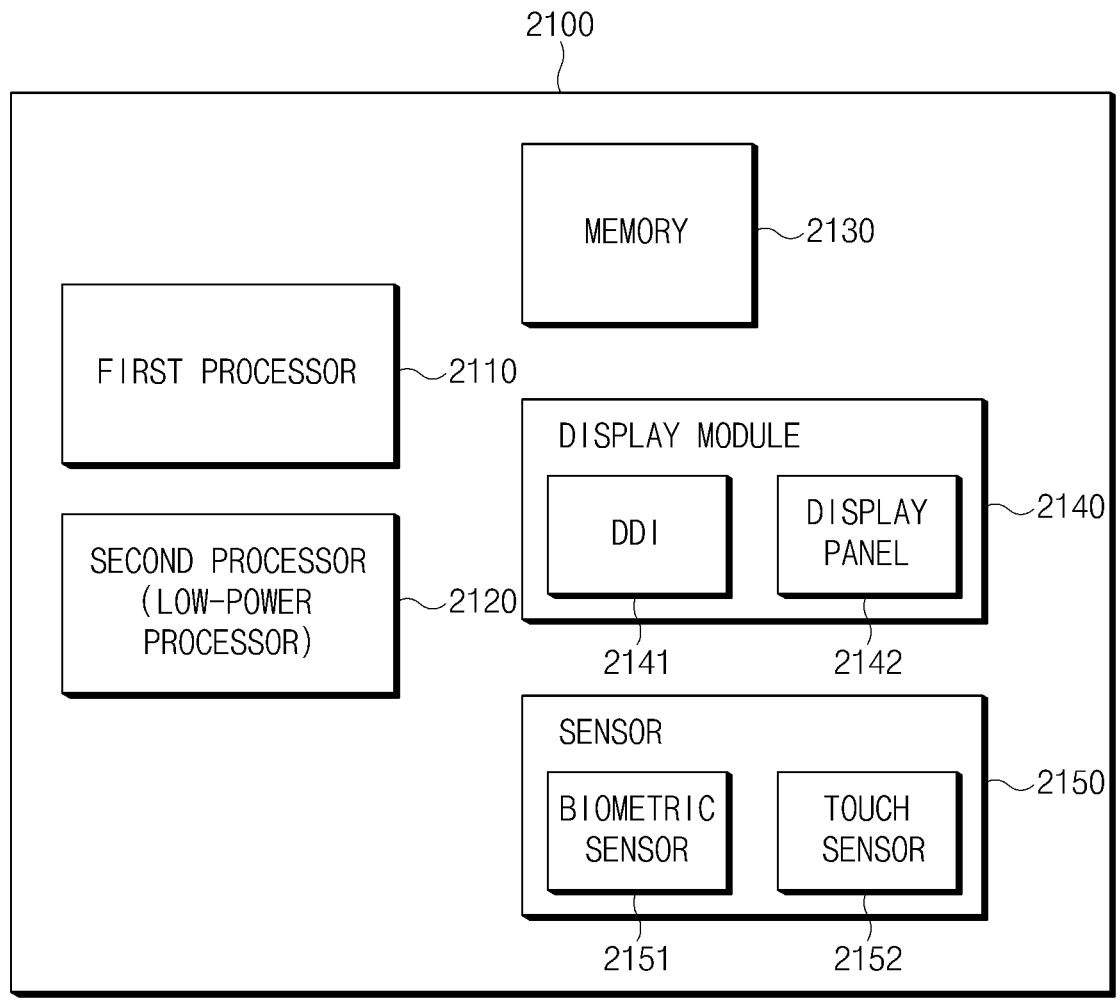
FIG. 21 is a block diagram of an electronic device, according to an embodiment of the present disclosure.

FIG. 21 is a block diagram of an electronic device, according to an embodiment of the present disclosure.

Referring to FIG. 21, an electronic device includes at least one processor (e.g., a first processor 2110 or a second processor 2120), a memory 2130, a display module 2140, and at least one sensor 2150. The first processor 2110 may control the overall operations of the electronic device. In the case where the electronic device is in a sleep state, the second processor 2120 (e.g., a low-power processor or a sensor controller) may process sensor information obtained through the at least one sensor 2150 or an input obtained from a user. The second processor 2120 may control a biometric sensor 2151, a touch sensor 2152, or the display module 2140 independently of the first processor 2110. The electronic device includes the memory 2130. The memory 2130 may include a normal area for storing a user application and the like, or a secure area for storing information sensitive to security such as information for fingerprint sensing and the like.

According to an embodiment of the present disclosure, the display module 2140 includes a display panel 2142 including a plurality of pixels and a display driving module 2141 that is configured to provide display information by controlling at least part of the plurality of pixels included in the display panel 2142. The sensor 2150 includes the biometric sensor 2151 (e.g., a fingerprint sensor) that senses the fingerprint of a user associated with the display module 2140 or the touch sensor 2152 that senses a touch of the user associated with the display module 2140. The biometric sensor 2151 may include an optical fingerprint sensor (e.g., an image sensor) that senses light, which is output by the display module as a light source.

According to an embodiment of the present disclosure, the at least one sensor 2150 may drive a plurality of pixels included in the display panel 2142 through the display driving module 2141 in response to the user input. The at least one sensor 2150 may control the display panel 2142 as needed. The biometric sensor 2151 may use the light emitted from the display by controlling the display panel 2142 to obtain biometric information of the user.

Figure 22:
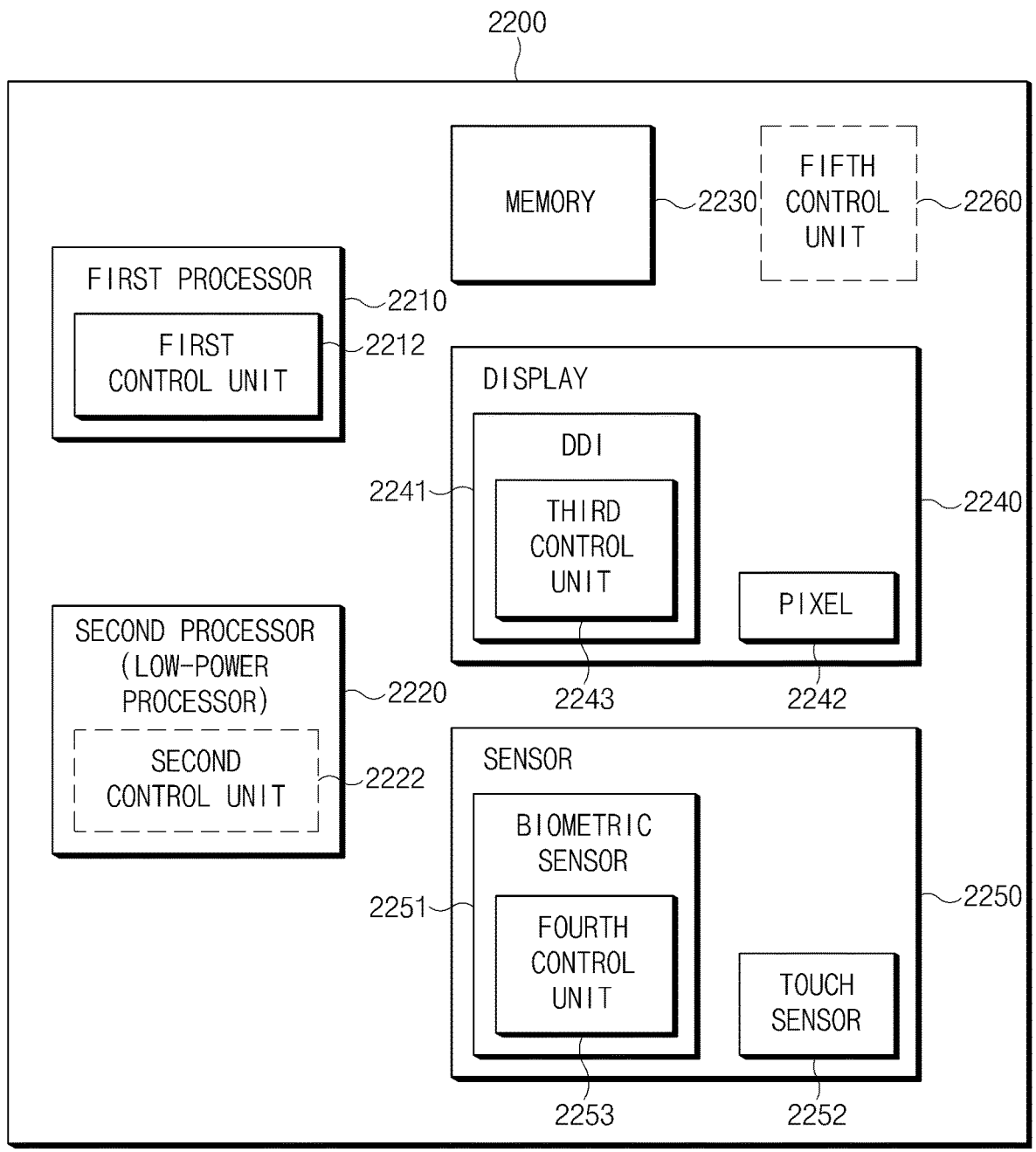
FIG. 22 is a block diagram of an electronic device, according to an embodiment of the present disclosure.

FIG. 22 is a block diagram of an electronic device, according to another embodiment of the present disclosure.

Referring to FIG. 22, an electronic device 2200 includes a first control unit 2212, a second control unit 2222, a third control unit 2243, a fourth control unit 2253, a fifth control unit 2260, and each controller may be included in a module (e.g., a first processor 2210, a second processor 2220, a DDI 2241, a biometric sensor 2251, and the like) included in the electronic device 2200. The electronic device 2200 may control the first processor 2210 by using the first control unit 2212 and may control the second processor 2220 by using the second control unit 2222. In addition, the electronic device 2200 may control modules, in which the third control unit 2243 and the fourth control unit 2253 are included, by using the third control unit 2243 and the fourth control unit 2253.

According to an embodiment of the present disclosure, the electronic device 2200 may control modules of the electronic device 2200 by using one controller. The electronic device 2200 may control the first control unit 2212, the second control unit 2222, the third control unit 2243, and the fourth control unit 2253 by using a main controller (e.g., the fifth control unit 2260). Furthermore, the electronic device 2200 may assign the main controller and may control other controllers under control of the assigned main controller. The electronic device 2200 may change/assign the main controller from the fifth control unit 2260 to the first control unit 2212 and may control other controllers by using the assigned main controller.

According to an embodiment of the present disclosure, the electronic device 2200 may directly control modules of the electronic device 2200 by using one controller. The electronic device 2200 may control the second processor 2220, the memory 2230, the display 2240, and/or at least one sensor 2250 by using the first control unit 2212 included in the first processor 2210. One controller may control the display 2240 and the at least one sensor 2250. In the case of an optical fingerprint sensor using a pixel 2242 of the display 2240 as a light source, the one controller may control the display 2240 and the sensor 2250 and biometric information of the user may be obtained.

As described above, according to an embodiment of the present disclosure, a slim shape of the electronic device 2200 may be achieved by disposing a light emitting module at a separate location such that the size or thickness of a fingerprint sensor decreases.

In addition, an embodiment of the present disclosure may provide a stable fingerprint sensing function regardless of whether a foreign object is present on the finger.

Figure 23:
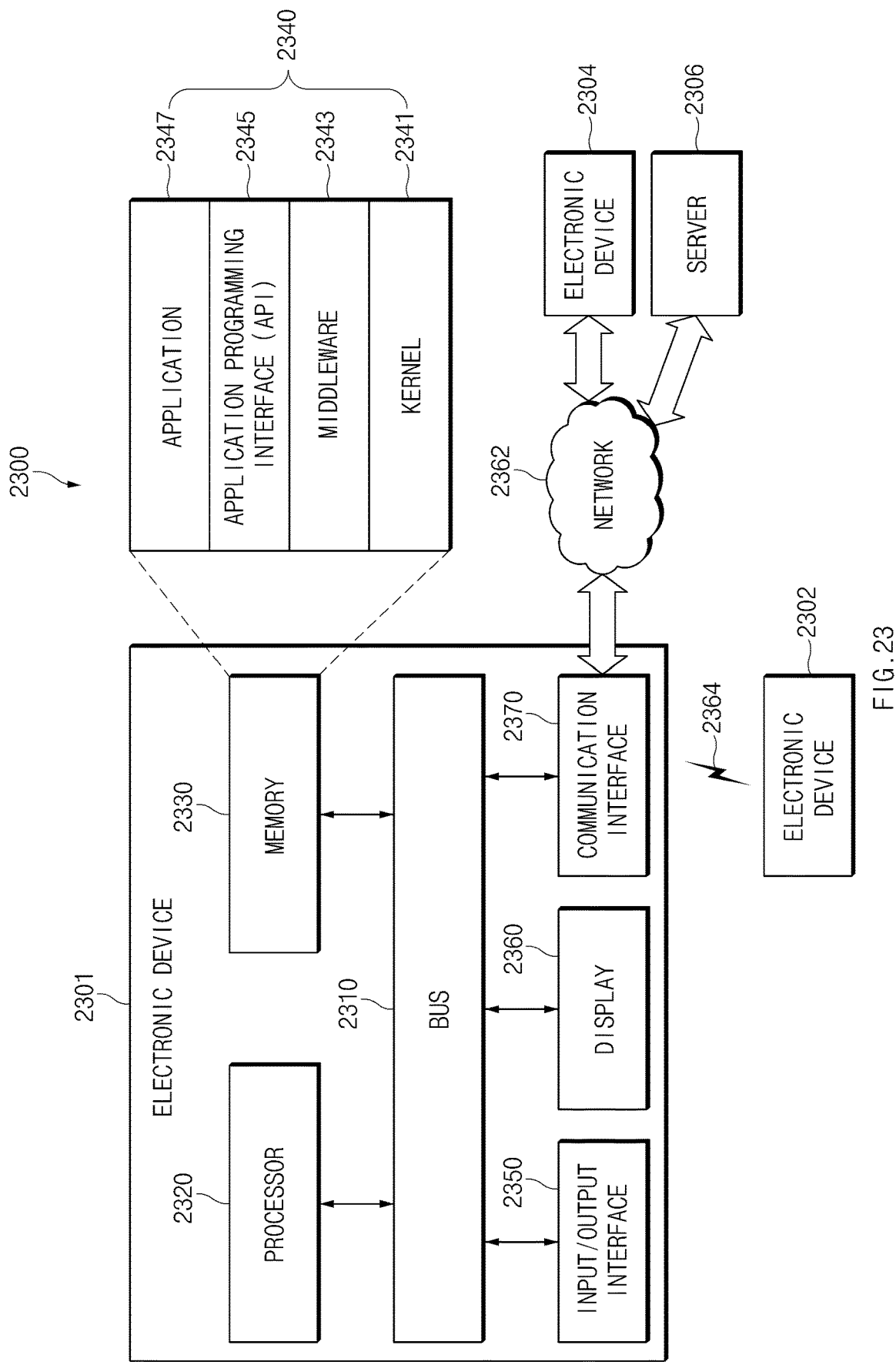
FIG. 23 is a block diagram of an electronic device in a network environment, according to an embodiment of the present disclosure.

FIG. 23 is a block diagram of an electronic device in a network environment according to an embodiment of the present disclosure.

Referring to FIG. 23, an electronic device 2301 and a first external electronic device 2302, a second external electronic device 2304, or a server 2306 may connect with each other through a network 2362 or local-area communication 2364. The electronic device 2301 includes a bus 2310, a processor 2320, a memory 2330, an input and output interface 2350, a display 2360, and a communication interface 2370. At least one of the components may be omitted from the electronic device 2301, or other components may be additionally included in the electronic device 2301.

The bus 2310 may be, for example, a circuit which connects the components 2320 to 2370 with each other and transmits a communication signal (e.g., a control message and/or data) between the components.

The processor 2320 may include one or more of a CPU, an AP, or a communication processor (CP). The processor 2320 may perform calculations or data processing about control and/or communication of at least another of the components of the electronic device 2301.

The memory 2330 may include a volatile and/or non-volatile memory. The memory 2330 may store, for example, a command or data associated with at least another of the components of the electronic device 2301. According to an embodiment of the present disclosure, the memory 2330 stores software and/or a program 2340. The program 2340 includes, for example, a kernel 2341, a middleware 2343, an application programming interface (API) 2345, and/or at least one application 2347. At least part of the kernel 2341, the middleware 2343, or the API 2345 may be referred to as an OS.

The kernel 2341 may control or manage, for example, system resources (e.g., the bus 2310, the processor 2320, or the memory 2330, and the like) used to execute an operation or function implemented in the other programs (e.g., the middleware 2343, the API 2345, or the application 2347). As the middleware 2343, the API 2345, the application 2347 accesses a separate component of the electronic device 2301, the kernel 2341 may provide an interface which may control or manage system resources.

The middleware 2343 may play a role as, for example, a go-between such that the API 2345 or the application 2347 communicates with the kernel 2341 to communicate data.

The middleware 2343 may process one or more work requests, received from the application 2347, in order of priority. The middleware 2343 may assign priorities which may use system resources (the bus 2310, the processor 2320, or the memory 2330, and the like) of the electronic device 2301 to at least one of the at least one application 2347. The middleware 2343 may perform scheduling or load balancing for the one or more work requests by processing the one or more work requests in order of the priority assigned to the at least one application 2347.

The API 2345 may be, for example, an interface in which the application 2347 controls a function provided from the kernel 2341 or the middleware 2343. The API 2345 may include at least one interface or function (e.g., a command) for file control, window control, image processing, or text control, and the like.

The input and output interface 2350 may play a role as, for example, an interface which may transmit a command or data input from a user or another external device to another component (or other components) of the electronic device 2301. Input and output interface 2350 may output an instruction or data received from another component (or other components) of the electronic device 2301 to the user or the other external device.

The display 2360 may include, for example, a liquid crystal display (LCD), an LED display, an organic LED (OLED) display, a microelectromechanical systems (MEMS) display, or an electronic paper display. The display 2360 may display, for example, a variety of content (e.g., text, images, videos, icons, or symbols, and the like) to the user. The display 2360 may include a touch screen, and may receive, for example, a touch, gesture, proximity, or a hovering input using an electronic pen or part of a body of the user.

The communication interface 2370 may establish communication between, for example, the electronic device 2301 and a first external electronic device 2302, a second external electronic device 2304, or a server 2306. The communication interface 2370 may connect to a network 2362 through wireless communication or wired communication and may communicate with the second external electronic device 2304 or the server 2306).

The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like as a cellular communication protocol. The wireless communication may include, for example, local-area communication 2364. The local-area communication 2364 may include, for example, at least one of wireless-fidelity (Wi-Fi) communication, Bluetooth™ (BT) communication, near field communication (NFC), or global navigation satellite system (GNSS) communication, and the like.

An magnetic stripe transaction (MST) module may generate a pulse based on transmission data using an electromagnetic signal and may generate a magnetic field signal based on the pulse. The electronic device 2301 may output the magnetic field signal to a POS system. The POS system may restore the data by detecting the magnetic field signal using an MST reader and converting the detected magnetic field signal into an electric signal.

The GNSS may include, for example, at least one of a global positioning system (GPS), a Glonass, a Beidou navigation satellite system (Beidou), or a Galileo (i.e., the European global satellite-based navigation system) according to an available area or a bandwidth, and the like. Hereinafter, the term "GPS" may be interchangeably with the term "GNSS". The wired communication may include at least one of, for example, universal serial bus (USB) communication, high definition multimedia interface (HDMI) communication, recommended standard 232 (RS-232) communication, or plain old telephone service (POTS) communication, and the like. The network 2362 may include a telecommunications network, for example, at least one of a computer network (e.g., a local area network (LAN) or a wide area network (WAN)), the Internet, or a telephone network.

Each of the first and second external electronic devices 2302 and 2304 may be the same as or different device from the electronic device 2301. According to an embodiment of the present disclosure, the server 2306 may include a group of one or more servers. All or some of operations executed in the electronic device 2301 may be executed in another electronic device or the first external electronic device 2302, the second external electronic device 2304, or the server 2306. If the electronic device 2301 should perform any function or service automatically or according to a request, it may request the first external electronic device 2302, the second external electronic device 2304, or the server 106 to perform at least part of the function or service, rather than executing the function or service for itself or in addition to the function or service. The first external electronic device 2302, the second external electronic device 2304, or the server 2306 may execute the requested function or the added function and may transmit the executed result to the electronic device 2301. The electronic device 2301 may process the received result without change or additionally and may provide the requested function or service. For this purpose, for example, cloud computing technologies, distributed computing technologies, or client-server computing technologies may be used.

Figure 24:
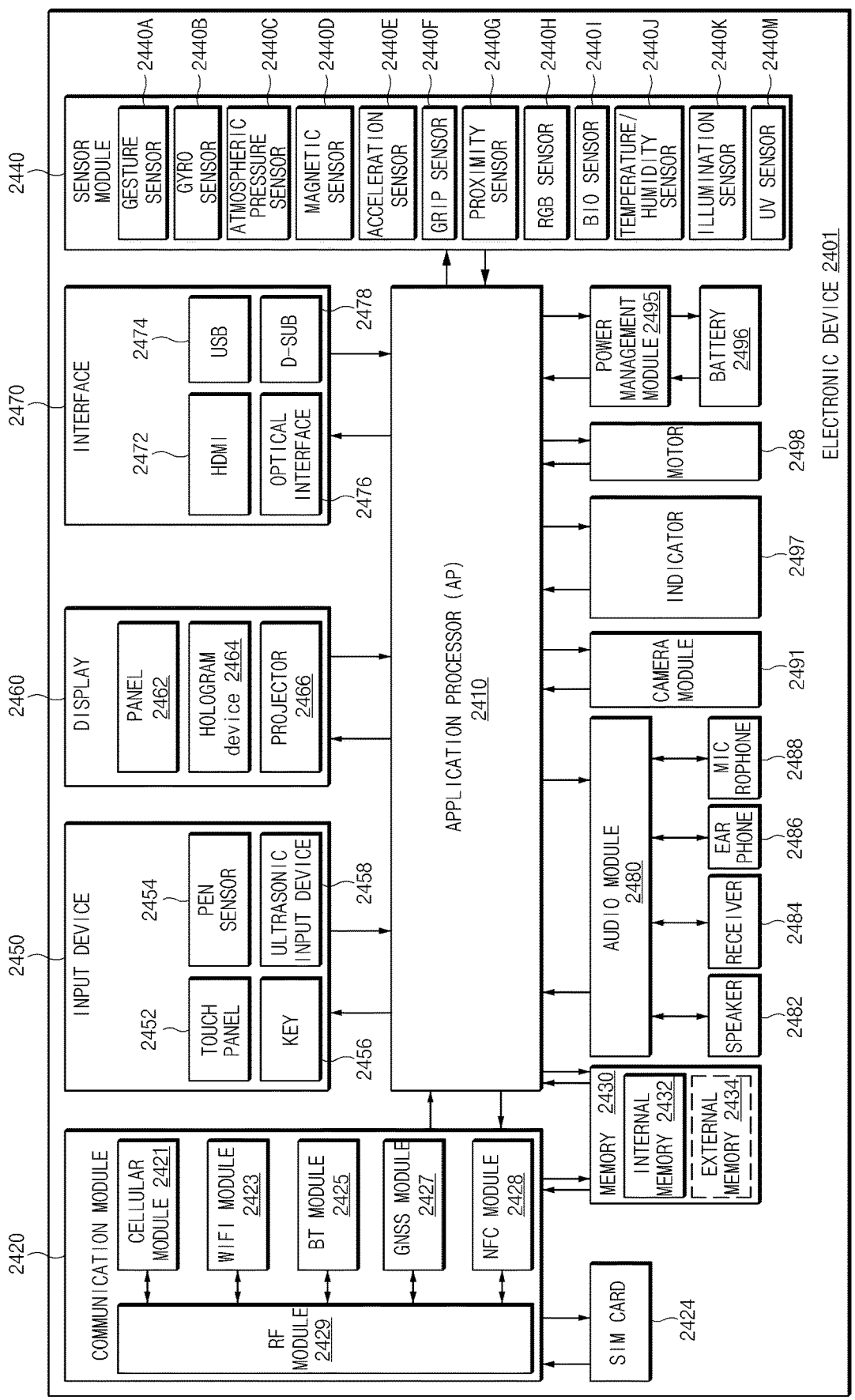
FIG. 24 is a block diagram of an electronic device, according to an embodiment of the present disclosure.

FIG. 24 is a block diagram of an electronic device according to an embodiment of the present disclosure.

Referring to FIG. 24, the electronic device 2401 includes one or more APs 2410, a communication module 2420, a subscriber identification module (SIM) card 2424, a memory 2430, a sensor module 2440, an input device 2450, a display 2460, an interface 2470, an audio module 2480, a camera module 2491, a power management module 2495, a battery 2496, an indicator 2497, and a motor 2498.

The AP 2410 may drive, for example, an operating system (OS) or an application program to control a plurality of hardware or software components connected thereto and may process and compute a variety of data. The AP 2410 may be implemented with, for example, a system on chip (SoC). According to an embodiment of the present disclosure, the AP 2410 may include a graphic processing unit (GPU) and/or an image signal processor. The AP 2410 may include at least some (e.g., a cellular module 2421) of the components shown in FIG. 24. The AP 2410 may load a command or data received from at least one of other components (e.g., a non-volatile memory) into a volatile memory to process the data and may store various data in a non-volatile memory.

The communication module 2420 includes, for example, the cellular module 2421, a wireless-fidelity (Wi-Fi) module 2423, a Bluetooth™ (BT) module 2425, a global navigation satellite system (GNSS) module 2427 (e.g., a GPS module, a Glonass module, a Beidou module, or a Galileo module), an NFC module 2428, and a radio frequency (RF) module 2429.

The cellular module 2421 may provide, for example, a voice call service, a video call service, a text message service, or an Internet service, and the like through a communication network. According to an embodiment of the present disclosure, the cellular module 2421 may identify and authenticate the electronic device 2401 in a communication network using the SIM card 2429. The cellular module 2421 may perform at least part of functions which may be provided by the AP 2410. The cellular module 2421 may include a CP.

The Wi-Fi module 2423, the BT module 2425, the GNSS module 2427, the NFC module 2428 may include, for example, a processor for processing data transmitted and received through the corresponding module. According to an embodiment of the present disclosure, at least some (e.g., two or more) of the cellular module 2421, the Wi-Fi module 2423, the BT module 2425, the GNSS module 2427, the NFC module 2428 may be included in one integrated chip (IC) or one IC package.

The RF module 2429 may transmit and receive, for example, a communication signal (e.g., an RF signal). The RF module 2427 may include, for example, a transceiver, a power amplifier module (PAM), a frequency filter, or a low noise amplifier (LNA), or an antenna, and the like. According to an embodiment of the present disclosure, at least one of the cellular module 2421, the Wi-Fi module 2423, the BT module 2425, the GNSS module 2427, the NFC module 2428 may transmit and receive an RF signal through a separate RF module.

The SIM card 2424 may include, for example, a card which includes a SIM and/or an embedded SIM. The SIM card 2424 may include unique identification information (e.g., an integrated circuit card identifier (ICCID)) or subscriber information (e.g., an international mobile subscriber identity (IMSI)).

The memory 2430 includes, for example, an internal memory 2432 or an external memory 2434. The internal memory 2432 may include at least one of, for example, a volatile memory (e.g., a dynamic random access memory (DRAM), a static RAM (SRAM), a synchronous dynamic RAM (SDRAM), and the like), or a non-volatile memory (e.g., a one-time programmable read only memory (OT-PROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory, and the like), a hard drive, or a solid state drive (SSD)).

The external memory 2434 may include a flash drive, for example, a compact flash (CF), a secure digital (SD), a micro-SD, a mini-SD, an extreme digital (xD), a multimedia car (MMC), or a memory stick, and the like. The external memory 2434 may operatively and/or physically connect with the electronic device 2401 through various interfaces.

The sensor module 2440 may measure, for example, a physical quantity or may detect an operation state of the electronic device 2401, and may convert the measured or detected information to an electric signal. The sensor module 2440 includes at least one of, for example, a gesture sensor 2440A, a gyro sensor 2440B, a barometer sensor 2440C, a magnetic sensor 2440D, an acceleration sensor 2440E, a grip sensor 2440F, a proximity sensor 2440G, a color sensor 2440H (e.g., red, green, blue (RGB) sensor), a biometric sensor 2440I, a temperature/humidity sensor 2440J, an illumination sensor 2440K, or an ultraviolet (UV) sensor 2440M. Additionally or alternatively, the sensor module 2440 may further include, for example, an e-nose sensor, an electromyography (EMG) sensor, an electroencephalogram (EEG) sensor an electrocardiogram (ECG) sensor, an infrared (IR) sensor, an iris sensor, and/or a fingerprint sensor 180, and the like. The sensor module 2440 may further include a control circuit for controlling at least one or more sensors included therein. According to an embodiment of the present disclosure, the electronic device 2401 may further include a processor configured to control the sensor module 2440, as part of the AP 2410 or to be independent of the AP 2410. While the AP 2410 is in a sleep state, the electronic device 2401 may control the sensor module 2440.

The input device 2450 includes, for example, a touch panel 2452, a (digital) pen sensor 2454, a key 2456, or an ultrasonic input device 2458. The touch panel 2452 may use at least one of, for example, a capacitive type, a resistive type, an infrared type, or an ultrasonic type. Also, the touch panel 2452 may further include a control circuit. The touch panel 2452 may further include a tactile layer and may provide a tactile reaction to a user.

The (digital) pen sensor 2454 may be, for example, part of the touch panel 2452 or may include a separate sheet for recognition. The key 2456 may include, for example, a physical button, an optical key, or a keypad. The ultrasonic input device 2458 may allow the electronic device 2401 to detect a sound wave using a microphone 2488 and to verify data through an input tool generating an ultrasonic signal.

The display 2460 includes a panel 2462, a hologram device 2464, or a projector 2466. The panel 2462 may be implemented to be, for example, flexible, transparent, or wearable. The panel 2462 and the touch panel 2452 may be integrated into one module. The hologram device 2464 may show a stereoscopic image in a space using interference of light. The projector 2466 may project light onto a screen to display an image. The screen may be positioned, for example, inside or outside the electronic device 2401. According to an embodiment of the present disclosure, the display 2460 may further include a control circuit for controlling the panel 2462, the hologram device 2464, or the projector 2466.

The interface 2470 includes, for example, a high-definition multimedia interface (HDMI) 2472, a universal serial bus (USB) 2474, an optical interface 2476, or a D-subminiature 2478. Additionally or alternatively, the interface 2470 may include, for example, a mobile high definition link (MHL) interface, an SD card/multimedia card (MMC) interface, or an infrared data association (IrDA) standard interface.

The audio module 2480 may convert a sound and an electric signal in dual directions. The audio module 2480 may process sound information input or output through, for example, a speaker 2482, a receiver 2484, an earphone 2486, or the microphone 2488, and the like.

The camera module 2491 may be a device which captures a still image and a moving image. According to an embodiment of the present disclosure, the camera module 2491 may include one or more image sensors (e.g., a front sensor or a rear sensor), a lens, an image signal processor (ISP), or a flash (e.g., an LED or a xenon lamp).

The power management module 2495 may manage, for example, power of the electronic device 2401. According to an embodiment of the present disclosure, the power management module 2495 may include a power management integrated circuit (PMIC), a charger IC or a battery gauge. The PMIC may have a wired charging method and/or a wireless charging method. The wireless charging method may include, for example, a magnetic resonance method, a magnetic induction method, or an electromagnetic method, and the like. An additional circuit for wireless charging, for example, a coil loop, a resonance circuit, or a rectifier, and the like may be further provided. The battery gauge may measure, for example, the remaining capacity of the battery 2496 and voltage, current, or temperature thereof while the battery 2496 is charged. The battery 2496 may include, for example, a rechargeable battery or a solar battery.

The indicator 2497 may display a specific state of the electronic device 2401 or part (e.g., the AP 2410) thereof, for example, a booting state, a message state, or a charging state, and the like. The motor 2498 may convert an electric signal into mechanical vibration and may generate vibration or a haptic effect, and the like. The electronic device 2401 may include a processing unit (e.g., a GPU) for supporting a mobile TV. The processing unit for supporting the mobile TV may process media data according to standards, for example, a digital multimedia broadcasting (DMB) standard, a digital video broadcasting (DVB) standard, or a MediaFlo™ standard, and the like.

Each of the above-mentioned elements of the electronic device according to an embodiment of the present disclosure may be configured with one or more components, and names of the corresponding elements may be changed according to the type of the electronic device. The electronic device may include at least one of the above-mentioned elements, some elements may be omitted from the electronic device, or other additional elements may be further included in the electronic device. Some of the elements of the electronic device may be combined with each other to form one entity, thereby making it possible to perform the functions of the corresponding elements in the same manner as before the combination.

Figure 25:
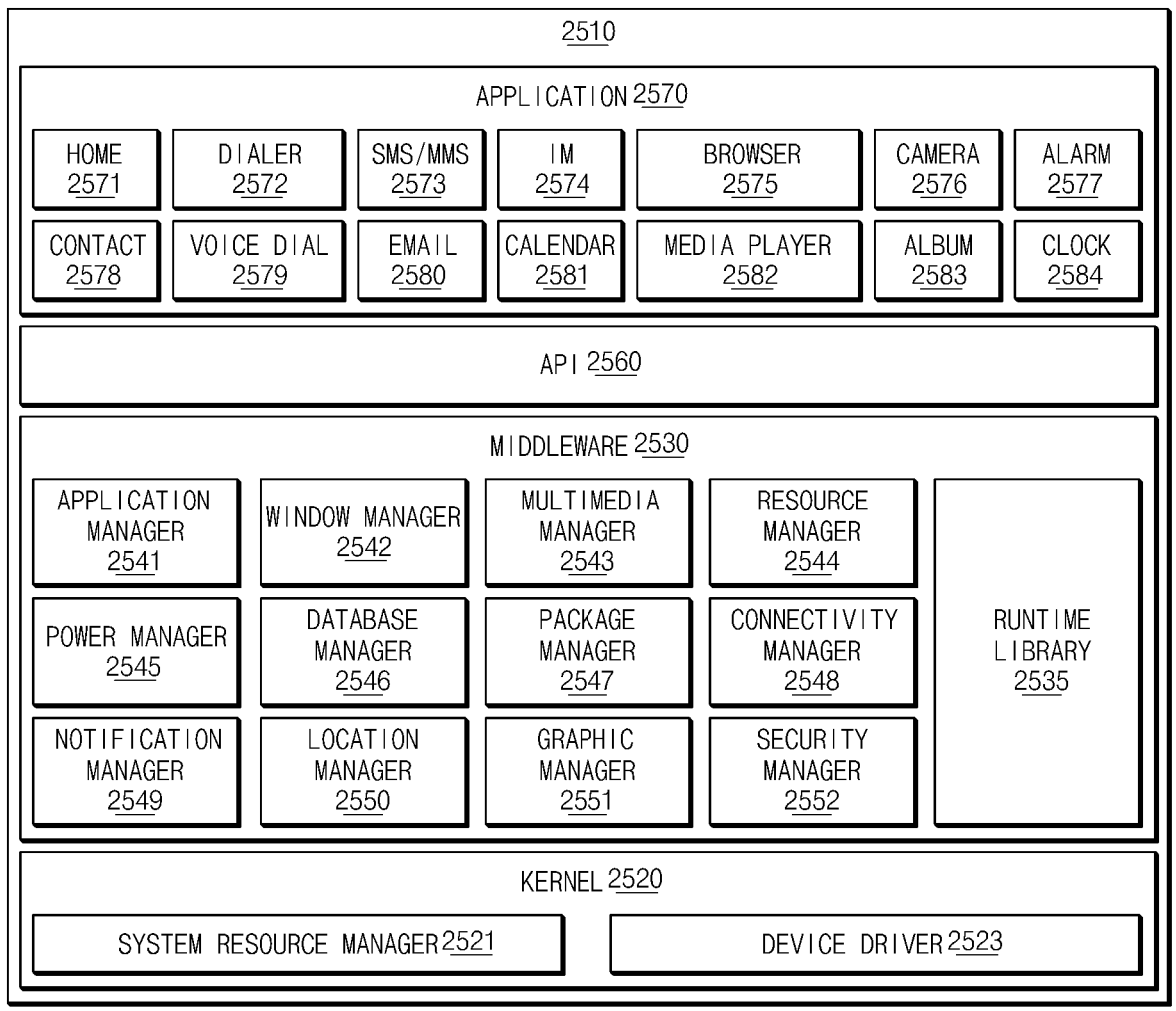
FIG. 25 is a block diagram of a program module, according to an embodiment of the present disclosure.

FIG. 25 is a block diagram of a program module, according to an embodiment of the present disclosure.

Referring to FIG. 25, the program module 2510 may include an operating system (OS) for controlling resources associated with an electronic device and/or various applications which are executed on the OS. The OS may be, for example, Android™, iOS™, Windows™, Symbian™, Tizen™, or Bada™, and the like.

The program module 2510 includes a kernel 2520, a middleware 2530, an application programming interface (API) 2560, and/or an applications 2570. At least part of the program module 2510 may be preloaded on the electronic device, or may be downloaded from a first external electronic device 2302, a second external electronic device 2304, or a server 2306.

The kernel 2520 includes, for example, a system resource manager 2521 and/or a device driver 2523. The system resource manager 2521 may control, assign, or collect, and the like system resources. According to an embodiment of the present disclosure, the system resource manager 2521 may include a process management unit, a memory management unit, or a file system management unit, and the like. The device driver 2523 may include, for example, a display driver, a camera driver, a BT driver, a shared memory driver, a USB driver, a keypad driver, a Wi-Fi driver, an audio driver, or an inter-process communication (IPC) driver.

The middleware 2530 may provide, for example, functions the applications 2570 needs in common, and may provide various functions to the applications 2570 through the API 2560 such that the applications 2570 efficiently uses limited system resources in the electronic device. According to an embodiment of the present disclosure, the middleware 2530 includes at least one of a runtime library 2535, an application manager 2541, a window manager 2542, a multimedia manager 2543, a resource manager 2544, a power manager 2545, a database manager 2546, a package manager 2547, a connectivity manager 2548, a notification manager 2549, a location manager 2550, a graphic manager 2551, a security manager 2552, or a payment manager.

The runtime library 2535 may include, for example, a library module used by a compiler to add a new function through a programming language while the application 2570 is executed. The runtime library 2535 may perform a function about input and output management, memory management, or an arithmetic function.

The application manager 2541 may manage, for example, a life cycle of at least one of the application 2570. The window manager 2542 may manage graphic user interface (GUI) resources used on a screen of the electronic device. The multimedia manager 2543 may determine a format utilized for reproducing various media files and may encode or decode a media file using a codec corresponding to the corresponding format. The resource manager 2544 may manage source codes of at least one of the application 2570, and may manage resources of a memory or a storage space, and the like.

The power manager 2545 may act together with, for example, a basic input/output system (BIOS) and the like, may manage a battery or a power source, and may provide power information utilized for an operation of the electronic device. The database manager 2546 may generate, search, or change a database to be used in at least one of the application 2570. The package manager 2547 may manage installation or update of an application distributed by a type of a package file.

The connectivity manager 2548 may manage, for example, wireless connection such as Wi-Fi connection or BT connection, and the like. The notification manager 2549 may display or notify events, such as an arrival message, an appointment, and proximity notification, by a method which does not disturb the user. The location manager 2550 may manage location information of the electronic device. The graphic manager 2551 may manage a graphic effect to be provided to the user or a user interface (UI) related to the graphic effect. The security manager 2552 may provide all security functions utilized for system security or user authentication, and the like. According to an embodiment of the present disclosure, when the electronic device has a phone function, the middleware 2530 may further include a telephony manager for managing a voice or video communication function of the electronic device.

The middleware 2530 may include a middleware module which configures combinations of various functions of the above-described components. The middleware 2530 may provide a module which specializes according to a type of OS to provide a differentiated function. Also, the middleware 2530 may dynamically delete some old components or may add new components.

The API 2560 may be, for example, a set of API programming functions, and may be provided with different components according to OSs. In case of Android™ or iOS™ one API set may be provided according to platforms. In case of Tizen™, two or more API sets may be provided according to platforms.

The application 2570 may include one or more of, for example, a home application 2571, a dialer application 2572, a short message service/multimedia message service (SMS/MMS) application 2573, an instant message (IM) application 2574, a browser application 2575, a camera application 2576, an alarm application 2577, a contact application 2578, a voice dial application 2579, an e-mail application 2580, a calendar application 2581, a media player application 2582, an album application 2583, a clock application 2584, a health care application (e.g., an application for measuring quantity of exercise or blood sugar level, and the like), or an environment information application (e.g., an application for providing atmospheric pressure information, humidity information, or temperature information), and the like.

According to an embodiment of the present disclosure, the application 2570 may include an information exchange application for exchanging information between the electronic device 2301 and the first external electronic device 2302 or the second external electronic device 2304. The information exchange application may include, for example, a notification relay application for transmitting specific information to the external electronic device or a device management application for managing the external electronic device.

The notification relay application may include a function of transmitting notification information, which is generated by other applications (e.g., the SMS/MMS application, the e-mail application, the health care application, or the environment information application of the electronic device) to the first external electronic device 2302 or the second external electronic device 2304. Also, the notification relay application may receive, for example, notification information from the external electronic device, and may provide the received notification information to the user of the electronic device.

The device management application may manage (e.g., install, delete, or update), for example, at least one (e.g., a function of turning on/off the external electronic device itself (or partial components) or a function of adjusting brightness (or resolution) of a display) of functions of the first external electronic device 2302 or the second external electronic device 2304 which communicates with the electronic device, an application which operates in the external electronic device, or a service (e.g., a call service or a message service) provided from the external electronic device.

According to an embodiment of the present disclosure, the application 2570 may include an application (e.g., the health card application of a mobile medical device) which is preset according to attributes of the first external electronic device 2302 or the second external electronic device 2304. The application 2570 may include an application received from the server 2306, the first external electronic device 2302, or the second external electronic device 2304. The application 2570 may include a preloaded application or a third party application which may be downloaded from a server. Names of the components of the program module 2510 may differ according to kinds of OS s.

According to an embodiment of the present disclosure, at least part of the program module 2510 may be implemented with software, firmware, hardware, or at least two or more combinations thereof. At least part of the program module 2510 may be implemented (e.g., executed) by, for example, a processor. At least part of the program module 2510 may include, for example, a module, a program, a routine, sets of instructions, or a process, and the like for performing one or more functions.

The term "module" as used herein may mean, for example, a unit including one of hardware, software, and firmware or two or more combinations thereof. The term "module" may be interchangeably used with, for example, the terms "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. The "module" may include at least one of an application-specific integrated circuit (ASIC) chip, field-programmable gate arrays (FPGAs), or a programmable-logic device, which is well known or will be developed in the future, for performing certain operations.

According to an embodiment of the present disclosure, at least part of a device (e.g., modules or the functions) or a method (e.g., operations) may be implemented with, for example, instructions stored in computer-readable storage media which have a program module. When the instructions are executed by a processor, one or more processors may perform functions corresponding to the instructions. The computer-readable storage media may be, for example, a memory.

The computer-readable storage media may include a hard disc, a floppy disk, magnetic media (e.g., a magnetic tape), optical media (e.g., a compact disc read only memory (CD-ROM) and a digital versatile disc (DVD)), magneto-optical media (e.g., a floptical disk), a hardware device (e.g., a ROM, a random access memory (RAM), or a flash memory, and the like), and the like. Also, the program instructions may include not only mechanical codes compiled by a compiler but also high-level language codes which may be executed by a computer using an interpreter and the like. The above-mentioned hardware device may be configured to operate as one or more software modules to perform operations according to an embodiment of the present disclosure, and vice versa.

Modules or program modules according to an embodiment of the present disclosure may include at least one or more of the above-mentioned components, some of the above-mentioned components may be omitted, or other additional components may be further included. Operations executed by modules, program modules, or other components may be executed by a successive method, a parallel method, a repeated method, or a heuristic method. Also, some operations may be executed in a different order or may be omitted, and other operations may be added.

The control unit may include a microprocessor or any suitable type of processing circuitry, such as one or more general-purpose processors (e.g., ARM-based processors), a digital signal processor (DSP), a programmable logic device (PLD), an ASIC, an FPGA, a graphical processing unit (GPU), a video card controller, etc. In addition, when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. In addition, a "processor" or "microprocessor" may be hardware in the present disclosure.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
   a light emitting module configured to radiate infrared light;
   a window disposed on the light emitting module and having a specific refractive index with respect to the infrared light, wherein the window includes a refraction part configured to reflect the infrared light inside the window in correspondence with the specific refractive index;
   a light change pattern formed in the window to correspond to an area in which the light emitting module is disposed and formed on a non-displaying area, and configured to change a propagation direction of the infrared light; and
   a fingerprint sensor disposed under the window and configured to obtain a fingerprint of a user based on a user input on the window using scattered light of the infrared light.

2. The electronic device of claim 1, wherein the window further includes a light transmitting layer in at least a partial area of the window, and
   wherein the light emitting module is configured to radiate the infrared light through the light transmitting layer.

3. The electronic device of claim 1, further comprising:
   a light guide member which is interposed between the window and the light emitting module.

4. An electronic device comprising:
   a window having a first refractive index with respect to light;
   a light emitting module disposed on one surface of the window and configured to radiate infrared light such that the infrared light is reflected inside the window in correspondence with the first refractive index;
   a light change pattern formed in the window to correspond to an area in which the light emitting module is disposed and formed on a non-displaying area, and configured to change a propagation direction of the infrared light;
   a connection member having a second refractive index and is interposed between the window and the light emitting module; and
   a fingerprint sensor disposed under the window and configured to obtain a fingerprint of a user based on a user input on the window using scattered light of the infrared light.

5. The electronic device of claim 4, further comprising:
   a light transmitting layer disposed under the window corresponding to an area in which the light emitting module is disposed and passing the infrared light such that the infrared light proceeds toward an inside of the window.

6. The electronic device of claim 4, wherein the light change pattern includes a scratch pattern.

7. The electronic device of claim 4, wherein the light change pattern includes:
   an optical member seated in a recess provided in an area under the window and configured to change a propagation path of the infrared light; or
   an optical member disposed in an area under the window and configured to change the propagation path of the infrared light.

8. The electronic device of claim 4, further comprising one of:
   a reflection plate disposed on a side surface of the window such that the infrared light is totally reflected toward an inside of the window by reflecting the infrared light; or
   a light guide member interposed between the light emitting module and a bottom surface of the window and configured to guide the infrared light toward the inside of the window.

9. The electronic device of claim 8, wherein the light guide member includes:
   a body part disposed such that one surface of the body part faces the light emitting module; and
   an adhesive member configured to fix the body part to the bottom surface of the window.

10. The electronic device of claim 4, further comprising:
    a light guide member including the light emitting module and disposed under the window to guide the infrared light toward an inside of the window,
    wherein the light guide member includes:
      a sensor substrate in which the light emitting module is seated;
      a body part surrounding the light emitting module; and
      an adhesive member configured to fix the lens body part to a bottom surface of the window.

11. The electronic device of claim 4, further comprising:
    a light guide member including the light emitting module and disposed under the window to guide the infrared light toward the inside of the window,
    wherein the light guide member includes:
      a fixing part of which one surface is disposed to face the window;
      a sensor substrate which is disposed in the fixing part and in which the light emitting module is mounted;
      a body part surrounding the light emitting module to guide the infrared light toward the window; and
      an adhesive member configured to fix the body part to a bottom surface of the window.

12. The electronic device of claim 4, wherein the light emitting module includes a plurality of light emitting modules disposed under one side of the window which is adjacent to the fingerprint sensor.

13. The electronic device of claim 4, further comprising:
    a proximity sensor disposed under one side of the window,
    wherein the light emitting module is disposed to:
      emit light of a specified wavelength band toward the inside of the window through one side of a light receiving unit or a light emitting unit of the proximity sensor, or
      emit light to a reflection member disposed on one side of the light receiving unit or the light emitting unit of the proximity sensor and allow light reflected by the reflection member to proceed while the light is totally reflected toward the inside of the window.

14. The electronic device of claim 4, further comprising:
a speaker housing disposed on one side of the window; and
a reflection area disposed on one side of the speaker housing,
wherein the light emitting module is disposed to allow the infrared light emitted to the reflection area to proceed while the infrared light emitted to the reflection area is totally reflected toward an inside of the window after being reflected in the reflection area.

15. The electronic device of claim 4, further comprising:
a speaker housing disposed under one side of the window,
wherein the light emitting module is disposed on one side of the speaker housing such that the infrared light emitted toward the inside of the window proceeds while being totally reflected.

16. The electronic device of claim 4, further comprising:
an illuminance sensor disposed under one side of the window,
wherein the light emitting module is disposed on one side of the illuminance sensor such that the infrared light emitted toward the inside of the window proceeds while being totally reflected.

17. The electronic device of claim 4, further comprising:
a display light emitting unit disposed in a periphery of the fingerprint sensor and configured to radiate a specific luminance or color with regard to an operation of the light emitting module.

18. A method of operating an electronic device, the method comprising:
receiving a user input;
activating a light emitting module disposed in an area under a periphery of a window such that infrared light is emitted while being reflected toward an inside of the window;
generating a fingerprint image by collecting the infrared light reflected on a surface of a finger disposed on the window while the infrared light is reflected inside the window and a light change pattern formed in the window to correspond to an area in which the light emitting module is disposed and formed on a non-displaying area, and configured to change a propagation direction of the infrared light; and
performing fingerprint authentication associated with the fingerprint image.

* * * * *